: US010736605B2

United States Patent
Heath et al.

(10) Patent No.: US 10,736,605 B2
(45) Date of Patent: Aug. 11, 2020

(54) DISPOSABLE EYEPIECE SYSTEM FOR AN ULTRASONIC EYE SCANNING APPARATUS

(71) Applicant: ArcScan, Inc., Golden, CO (US)

(72) Inventors: Gary B. Heath, Littleton, CO (US); Andrew K. Levien, Morrison, CO (US); John D. Watson, Evergreen, CO (US)

(73) Assignee: ArcScan, Inc., Golden, CO (US)

( * ) Notice: Subject to any disclaimer, the term of this patent is extended or adjusted under 35 U.S.C. 154(b) by 438 days.

(21) Appl. No.: 14/630,101

(22) Filed: Feb. 24, 2015

(65) Prior Publication Data
US 2015/0238166 A1 Aug. 27, 2015

Related U.S. Application Data

(60) Provisional application No. 61/943,667, filed on Feb. 24, 2014.

(51) Int. Cl.
*A61B 8/10* (2006.01)
*A61B 8/00* (2006.01)
*A61B 8/14* (2006.01)

(52) U.S. Cl.
CPC .......... *A61B 8/10* (2013.01); *A61B 8/14* (2013.01); *A61B 8/4209* (2013.01); *A61B 8/4422* (2013.01)

(58) Field of Classification Search
CPC .. A61B 3/125; A61B 8/00; A61B 8/10; A61B 8/44; A61B 8/14; G01S 7/52079

(Continued)

(56) References Cited

U.S. PATENT DOCUMENTS 3,371,660 A    3/1968  Benson
3,821,891 A *  7/1974  Collins ............... A61B 3/1005
                                                         351/211

(Continued)

FOREIGN PATENT DOCUMENTS

CA       2295431       7/2001
CA       2299483       7/2001

(Continued)

OTHER PUBLICATIONS

Angelson et al. "Which transducer array is best?" European Journal of Ultrasound, 1995, vol. 2., pp. 151-164.

(Continued)

*Primary Examiner* — Kristina M Deherrera
(74) *Attorney, Agent, or Firm* — Sheridan Ross P.C.

(57) ABSTRACT

A disposable eye piece system, including the eye piece and other disposable components, for a precision ultrasonic scanning apparatus is disclosed. The eye piece includes a fill port, a vent port and a drain port molded into the base of the eye piece. An RF Identification chip may be molded into the plastic base of the eye piece or, alternately into the conformable face seal of the eye piece. The components of a disposable eye piece system form an integrated disposable package that can be assembled, packaged, transported and used while maintaining the eye piece and saline solution in a sterile condition. The protective shipping container 1) protects the eye piece from damage, human contact and exposure to ambient air during shipping and storage and 2) allows the scanning physician or technician to attach the eye piece to the scanning machine without compromising the sterile condition of the eye piece.

17 Claims, 13 Drawing Sheets

(58) Field of Classification Search
USPC .................. 351/205–247; 600/407, 437, 459
See application file for complete search history.

(56) References Cited

U.S. PATENT DOCUMENTS

| | | | |
|---|---|---|---|
| 3,997,793 A | 12/1976 | Rogers et al. | |
| 4,092,867 A | 6/1978 | Matzuk | |
| 4,114,214 A | 9/1978 | VonHeck | |
| 4,154,114 A | 5/1979 | Katz | |
| 4,183,249 A | 1/1980 | Anderson | |
| 4,206,763 A | 6/1980 | Pedersen | |
| 4,227,780 A | 10/1980 | Ohta et al. | |
| 4,233,988 A | 11/1980 | Dick | |
| 4,245,250 A | 1/1981 | Tiemann | |
| 4,282,755 A | 8/1981 | Gardineer et al. | |
| 4,347,213 A | 8/1982 | Rogers | |
| 4,484,569 A | 11/1984 | Driller et al. | |
| 4,493,877 A | 1/1985 | Burnett | |
| 4,545,385 A | 10/1985 | Pirschel | |
| 4,550,607 A | 11/1985 | Maslak et al. | |
| 4,564,018 A | 1/1986 | Hutchison et al. | |
| 4,807,634 A | 2/1989 | Enjoji et al. | |
| 4,815,047 A | 3/1989 | Hart | |
| 4,817,432 A | 4/1989 | Wallace et al. | |
| 4,823,801 A | 4/1989 | Sakane | |
| 4,858,124 A | 8/1989 | Lizzi et al. | |
| 4,858,613 A | 8/1989 | Fry et al. | |
| 4,930,512 A | 6/1990 | Henriksen et al. | |
| 4,932,414 A | 6/1990 | Coleman et al. | |
| 5,029,587 A | 7/1991 | Baba et al. | |
| 5,079,786 A | 1/1992 | Rojas | |
| 5,103,517 A | 4/1992 | Krouskop | |
| 5,116,114 A | 5/1992 | Nakamura et al. | |
| 5,152,746 A | 10/1992 | Atkinson et al. | |
| 5,293,871 A | 3/1994 | Reinstein et al. | |
| 5,331,962 A | 7/1994 | Coleman et al. | |
| 5,369,454 A | 11/1994 | Reinstein et al. | |
| 5,387,180 A | 2/1995 | Lehmer | |
| 5,460,179 A | 10/1995 | Okunuki et al. | |
| 5,474,070 A | 12/1995 | Ophir et al. | |
| 5,487,388 A | 1/1996 | Rello et al. | |
| 5,517,991 A | 5/1996 | Herrmann et al. | |
| 5,551,432 A | 9/1996 | Iezzi | |
| 5,556,169 A | 9/1996 | Parrish et al. | |
| 5,614,099 A | 3/1997 | Hirose et al. | |
| 5,626,150 A | 5/1997 | Johnson et al. | |
| 5,626,594 A | 5/1997 | Smith | |
| 5,647,367 A | 7/1997 | Lum et al. | |
| 5,671,739 A | 9/1997 | Darrow et al. | |
| 5,776,068 A | 7/1998 | Silverman et al. | |
| 5,826,583 A | 10/1998 | Wood | |
| 5,832,550 A | 11/1998 | Hauger et al. | |
| 5,855,207 A | 1/1999 | Moenning et al. | |
| 5,906,205 A | 5/1999 | Hiebert | |
| 5,966,763 A | 10/1999 | Thomas et al. | |
| 5,971,006 A | 10/1999 | Seigerschmidt | |
| 6,053,613 A | 4/2000 | Wei et al. | |
| 6,145,143 A | 11/2000 | Hicks et al. | |
| 6,154,204 A | 11/2000 | Thompson et al. | |
| 6,198,956 B1 | 3/2001 | Dunne | |
| 6,315,727 B1 | 11/2001 | Coleman et al. | |
| 6,318,372 B1 | 11/2001 | Hiebert | |
| 6,334,227 B1 | 1/2002 | Larger | |
| 6,374,439 B2 | 4/2002 | Heimbrock et al. | |
| 6,451,008 B1 | 9/2002 | Frey et al. | |
| 6,460,207 B1 | 10/2002 | Papay et al. | |
| 6,487,447 B1 | 11/2002 | Weimann et al. | |
| 6,491,637 B2 | 12/2002 | Foster et al. | |
| 6,574,813 B2 | 6/2003 | Bolden et al. | |
| 6,629,929 B1 | 10/2003 | Jago et al. | |
| 6,684,433 B2 | 2/2004 | Giori et al. | |
| 6,780,153 B2 | 8/2004 | Angelsen et al. | |
| 6,837,855 B1 | 1/2005 | Puech | |
| 6,868,569 B2 | 3/2005 | VanSteenburg | |
| 6,887,203 B2 | 5/2005 | Phillips et al. | |
| 6,923,767 B2 | 8/2005 | Saied et al. | |
| 6,981,417 B1 | 1/2006 | Oravecz | |
| 7,048,690 B2 | 5/2006 | Coleman et al. | |
| 7,168,116 B2 | 1/2007 | Reger et al. | |
| 7,237,898 B1 | 7/2007 | Hohla | |
| 7,356,905 B2 | 4/2008 | Ketterling et al. | |
| 7,451,507 B2 | 11/2008 | Brinkerhoff et al. | |
| 7,454,024 B2 | 11/2008 | Ketterling et al. | |
| 7,474,041 B2 | 1/2009 | Ketterling et al. | |
| 7,480,058 B2 | 1/2009 | Zhao et al. | |
| 7,611,507 B2 * | 11/2009 | Raksi | A61F 9/009 606/4 |
| 7,708,342 B2 | 5/2010 | Leach | |
| 7,920,909 B2 | 4/2011 | Lyon et al. | |
| 8,064,989 B2 | 11/2011 | Brown et al. | |
| 8,068,647 B2 | 11/2011 | Lin | |
| 8,115,935 B2 | 2/2012 | Everett et al. | |
| 8,317,709 B2 | 11/2012 | Eilers et al. | |
| 8,475,384 B2 | 7/2013 | Hart et al. | |
| 8,496,588 B2 | 7/2013 | Eilers et al. | |
| 8,510,883 B2 | 8/2013 | Eilers et al. | |
| 8,732,878 B2 | 5/2014 | Eilers et al. | |
| 8,758,252 B2 | 6/2014 | Eilers et al. | |
| 8,824,743 B2 | 9/2014 | Daigle | |
| 9,039,623 B2 | 5/2015 | Eilers et al. | |
| 2001/0020200 A1 | 9/2001 | Das et al. | |
| 2002/0085173 A1 | 7/2002 | Schippert et al. | |
| 2002/0143252 A1 | 10/2002 | Dunne et al. | |
| 2003/0004416 A1 | 1/2003 | Phillips et al. | |
| 2003/0142269 A1 | 7/2003 | Cumming | |
| 2004/0200754 A1 * | 10/2004 | Hagemeier | A61F 9/0017 206/570 |
| 2004/0220478 A1 | 11/2004 | Wallace et al. | |
| 2005/0008527 A1 * | 1/2005 | Bayer | A61L 2/26 422/1 |
| 2005/0067494 A1 | 3/2005 | Ito et al. | |
| 2005/0120479 A1 | 6/2005 | Habashi et al. | |
| 2005/0143638 A1 | 6/2005 | Johnson et al. | |
| 2006/0029525 A1 | 2/2006 | Laugharn, Jr. et al. | |
| 2006/0058717 A1 | 3/2006 | Hui et al. | |
| 2006/0074287 A1 | 4/2006 | Neumann et al. | |
| 2006/0106313 A1 | 5/2006 | Hobson | |
| 2006/0241533 A1 | 10/2006 | Geller | |
| 2006/0288487 A1 | 12/2006 | Roleder et al. | |
| 2007/0051362 A1 | 3/2007 | Sullivan et al. | |
| 2007/0083995 A1 | 4/2007 | Purdy et al. | |
| 2007/0239020 A1 | 10/2007 | Iinuma et al. | |
| 2007/0239030 A1 | 10/2007 | Prager et al. | |
| 2007/0276233 A1 | 11/2007 | Besson et al. | |
| 2008/0097214 A1 | 4/2008 | Meyers et al. | |
| 2008/0146939 A1 | 6/2008 | McMorrow et al. | |
| 2008/0161696 A1 | 7/2008 | Schmitt et al. | |
| 2009/0088623 A1 | 4/2009 | Vortman et al. | |
| 2009/0192389 A1 * | 7/2009 | Eilers | A61B 3/1005 600/459 |
| 2009/0234369 A1 | 9/2009 | Bax et al. | |
| 2009/0318758 A1 | 12/2009 | Farr et al. | |
| 2010/0031448 A1 | 2/2010 | Hijkema | |
| 2010/0217125 A1 | 8/2010 | Kadokura et al. | |
| 2010/0229306 A1 | 9/2010 | Reeder et al. | |
| 2010/0249562 A1 | 9/2010 | Zhang | |
| 2010/0321697 A1 | 12/2010 | Zheng et al. | |
| 2011/0172511 A1 | 7/2011 | Peterson et al. | |
| 2012/0053459 A1 | 3/2012 | Eilers et al. | |
| 2012/0209118 A1 * | 8/2012 | Warnking | A61B 8/085 600/439 |
| 2012/0320368 A1 | 12/2012 | Jiao | |
| 2013/0072755 A1 | 3/2013 | Papania et al. | |
| 2013/0085370 A1 | 4/2013 | Friedman | |
| 2013/0102922 A1 * | 4/2013 | Gooding | A61B 3/14 600/558 |
| 2013/0144171 A1 | 6/2013 | Watson | |
| 2013/0237826 A1 | 9/2013 | Levien | |
| 2013/0310692 A1 | 11/2013 | Watson et al. | |
| 2014/0009741 A1 | 1/2014 | Levien et al. | |
| 2014/0249422 A1 | 9/2014 | Eilers et al. | |
| 2014/0268037 A1 * | 9/2014 | Siminou | A61B 3/0083 351/205 |
| 2014/0371589 A1 | 12/2014 | Nakabayashi | |

(56) References Cited

U.S. PATENT DOCUMENTS

| 2015/0031998 | A1 | 1/2015 | Kyono et al. |
| 2015/0265243 | A1 | 9/2015 | Kelly |
| 2017/0119345 | A1 | 5/2017 | Levien et al. |

FOREIGN PATENT DOCUMENTS

| CA | 2395203 | 7/2001 |
| CA | 2409234 | 4/2004 |
| JP | 2006-149001 | 6/2006 |
| WO | WO 2013/103167 | 7/2013 |

OTHER PUBLICATIONS

Binder, "SL-OCT and Ultrasound Support the Need for New Phakic IOL Sizing Strategies," Euro Times, Mar. 2007, p. 11.
Coleman et al., "Ultrasonography of the Eye and Orbit," Second Edition, published by Lippincott Williams & Wilkins, 2006, pp. 1-186.
Izatt et al., "Theory of Optical Coherence Tomography," Chap. 2 of "Optical Coherence Tomography Technology and Applications," Drexler and Fujimoto eds, ISBN:978-3-540-77549-2, 2008, pp. 47-72.
Ketterling, "Design and Fabrication of a 40-MHz Annular Array Transducer," IEEE Transactions on Ultrasonics, Ferroelectrics, and Frequency Control, Apr. 2005, vol. 52, No. 4, pp. 672-681.
Ketterling, "Operational Verification of a 40-MHz Annular Array Transducer," IEEE Transactions on Ultrasonics, Ferroelectrics, and Frequency Control, Mar. 2006, vol. 53, No. 3, pp. 623-630.
Mamou, "Chirp-Coded Excitation Imaging With a High-Frequency Ultrasound Annular Array," IEEE Transactions on Ultrasonics, Ferroelectrics, and Frequency Control, Feb. 2008, vol. 55, No. 2, pp. 508-513.
Pinero et al., "Equivalence, Differences Identified in Biometric Analysis," Cataract & Refractive Surgery Today, Mar. 2008, vol. 3, No. 12, pp. 46-49.
Reinstein et al., "Repeatability of Layered Corneal Pachymetry With the Artemis Very High Frequency Digital Ultrasound Arc-Scanner," J. Refractive Surg., vol. 26(9), 2009, original article, 6 pages.
Reinstein, "Subsurface Screening for Keratoconus—Accurate Measurements of the Epithelial and Stromal Layers Aid in Diagnosis," Cataract and Refractive Surgery Today, May 2007, pp. 88-89.
Roholt, "Sizing the Visian ICL," Cataract and Refractive Surgery Today, May 2007, p. 50.
Silverman et al., "Improved System for Sonographic Imaging and Biometry of the Cornea," J. Ultrasound Med., 1997, vol. 16, pp. 117-124.
International Search Report and Written Opinion for International (PCT) Patent Application No. PCT/US2015/017213, dated May 19, 2015 16 pages.
U.S. Appl. No. 15/048,706, filed Feb. 19, 2016, Levien et al.
U.S. Appl. No. 15/081,549, filed Mar. 25, 2016, Eilers et al.
"Campbell-Walsh Urology," Tenth Edition, W.B. Saunders, 2012, ISBN 978-1-4160-6911-9, abstract only, 2 pages.
"Information for Manufacturers Seeking Marketing Clearance of Diagnostic Ultrasound Systems and Transducers", 2008, Center for Devices and Radiological Health, 68 pages.
Kim et al., "20 MHz/40 MHz Dual Element Transducers for High Frequency Harmonic Imaging," IEEE Transactions on Ultrasonics, Ferroelectrics and Frequency Control, 2008, vol. 55(12), pp. 2683-2691, 25 pages.
Misaridis et al., "Use of Modulated Excitation Signals in Medical Ultrasound. Part I: Basic Concepts and Expected Benefits," IEEE Transactions on Ultrasonics, Ferroelectrics, and Frequency Control, 2005, vol. 52(2), pp. 177-191.
Sanchez et al., "A Novel Coded Excitation Scheme to Improve Spatial and Contrast Resolution of Quantitative Ultrasound Imaging," IEEE Transactions on Ultrasonics, Ferroelectrics, and Frequency Control, 2009, vol. 56(10), pp. 2111-2123, abstract only, 1 page.
Silverman et al., "High-Frequency Ultrasonic Imaging of the Anterior Segment Using an Annular Array Transducer," Ophthalmology, 2007, vol. 114(4), pp. 816-822, 15 pages.
Song et al., "Coded excitation for ultrasound tissue harmonic imaging," Ultrasonics, in revised form Dec. 18, 2009, retrieved from journal homepage: www.elsevier.com/locate/ultras, pp. 1-7.
International Preliminary Report on Patentability for International (PCT) Patent Application No. PCT/US2015/017213, dated Sep. 9, 2016 15 pages.

* cited by examiner

DISPOSABLE EYEPIECE SYSTEM FOR AN ULTRASONIC EYE SCANNING APPARATUS

CROSS-REFERENCE TO RELATED APPLICATIONS

This application claims the benefits, under 35 U.S.C. § 119(e), of U.S. Provisional Application Ser. No. 61/943,667 entitled "Disposable Eyepiece System for an Ultrasonic Eye Scanning Apparatus" filed Feb. 24, 2014 which is incorporated herein by reference.

FIELD OF INVENTION

The present invention relates to ultrasonic imaging of biological materials such as the cornea and natural lens of the eye and in particular relates to a disposable eye piece system.

BACKGROUND OF THE INVENTION

Ultrasonic imaging has found use in accurate measurement of structures of the eye such as, for example, the cornea and lens capsule. Such measurements provide an ophthalmic surgeon valuable information that can be used to guide various surgical procedures for correcting refractive errors such as LASIK and lens replacement. They also provide diagnostic information after surgery has been performed to assess the geometrical location of corneal features such as the LASIK scar and lens features such as lens connection, position and orientation. This allows the surgeon to assess post surgical changes in the cornea or lens and to take steps to correct any problems that develop.

Except for on-axis measurements, dimensions and locations of eye components behind the iris cannot be fully determined by optical means. Ultrasonic imaging in the frequency range of about 5 MHz to about 80 MHz can be applied to make accurate and precise measurements of structures of the eye, such as the cornea, lens capsule, lens ciliary muscle and the like.

Ultrasonic imaging has been used in corneal procedures such as LASIK to make accurate and precise images and maps of cornea thickness which include epithelial thickness, Bowman's layer and images of LASIK flaps. These images have a resolution of a few microns.

New procedures such as implantation of accommodative lenses may provide nearly perfect vision without spectacles or contact lenses. Implantation of accommodative lenses requires precision measurements of, for example, the position and width of the natural lens for successful lens powering and implantation. Ultrasonic imaging can be used to provide the required accurate images of the natural lens especially where the zonules attach the natural lens to the ciliary body which is well off-axis and behind the iris and therefore not readily accessible to optical imaging.

Other new procedures such as implantation of stents in or near the suprachoroid space may provide part or all of a treatment for glaucoma. Ultrasonic imaging can be used to provide the required accurate images in the corner of the eye between the sclera and the iris (in the suprachoroidal space) which is well off-axis and substantially inaccessible to optical imaging.

Such measurements can also provide ophthalmic researchers with valuable information that can be used 1) in the design of accommodative lenses, 2) provide ophthalmic surgeons with valuable information that can be used to guide various surgical procedures performed on the lens, 3) in the design of glaucoma stents, 4) provide ophthalmic surgeons with valuable information that can be used to guide placement of stents for treatment of glaucoma.

Recent advances in ultrasonic imaging have allowed images of substantially the entire lens capsule to be made. This has opened up the ability of diagnostic devices to assist in both research of lens implantation devices and strategies, and to planning, executing and follow-up diagnostics for corrective lens surgery including specialty procedures such as glaucoma and cataract treatments as well as implantation of clear intraocular lenses including accommodative lenses.

The use of ultrasonic imaging of important features of the eye for lens implantation is discussed, for example, in U.S. Pat. No. 7,048,690, which is herein incorporated by reference in its entirety. U.S. Pat. No. 7,048,690 does not include techniques for imaging the posterior surface of the lens capsule and so cannot be used to compute the volume of a lens capsule. Means for obtaining a full image of the lens capsule are disclosed in US Publication No. 2010/0,004,538 and U.S. Pat. No. 8,317,709, which are herein incorporated by reference in their entirety.

The ultrasonic system described herein is capable of accurately moving an ultrasound transducer with respect to a known reference point on a patient's head. Further improvements allow for tracking of unintended eye motions during scanning as disclosed in US Publication No. 2013/0,310,692, which is herein incorporated by reference in its entirety.

It must be appreciated that ultrasonic imaging requires a liquid medium to be interposed between the object being imaged and the transducer, which requires in turn that the eye, the transducer, and the path between them be at all times be immersed in a liquid medium wherein the acoustic impedance is substantially continuous. Concern for safety of the cornea introduces the practical requirement that the liquid medium be either pure water or normal saline water solution.

An eyepiece serves to complete a continuous acoustic path for ultrasonic scanning, that path extending from the transducer to the surface of the patient's eye. The eyepiece also separates the water in which the patient's eye is immersed from the water in the chamber in which the ultrasound transducer and guide track assembly are contained. Finally, the eyepiece provides a steady rest for the patient and helps the patient to remain steady during a scan. To be practical, the eyepiece should be free from frequent leakage problems, should be comfortable to the patient and its manufacturing cost should be low since it should be replaced for every new patient.

Another ultrasound scanning method is known as Ultrasound BioMicroscopy (UBM) which is implemented as a hand-held device that can capture anterior segment images using a transducer to emit short acoustic pulses ranging from about 20 to about 80 MHz. This type of ultrasound scanner is also called a sector scanner. The device can be used to capture reflected acoustic pulses using an open scleral shell filled with saline, which is a scleral shell filled with soft contact lens saline which is placed on an anesthetized eye and the UBM probe is held in the saline. Alternately, a special cup, known as the Prager cup may be used. This cup or bag/balloon technique using the ClearScan cover (ESI Inc., Plymouth, Minn.) utilizes a sterile, single-use water-filled bag covering the end of the UBM probe. A flexible collar, also serving as a valve to adjust internal bag pressure, secures to the ultrasound probe and creates a watertight seal. The water-filled bag conforms to the contour of the eye and inserting the probe into the bag creates positive pressure keeping the swiveling probe tip from making contact with the eye. The UBM method is capable of making qualitative ultrasound images of the anterior segment of the eye but cannot unambiguously make accurate, precision, comprehensive, measurable images of the cornea, lens or other components of the eye.

There remains, therefore, a need for integrated, closed system disposable packages that include an eye piece, a saline reservoir and associated tubing to ensure safe, precision ultrasonic scanning.

SUMMARY OF THE INVENTION

These and other needs are addressed by the present disclosure. The various embodiments and configurations of the present disclosure are directed generally to ultrasonic imaging of biological materials such as the cornea and lens of the eye and in particular directed to a disposable eye piece system for a precision ultrasonic scanning apparatus.

A disposable eye piece system is disclosed which includes the eye piece itself and other components. The eye piece includes a number of new features and construction details not previously disclosed. The eye piece includes a fill port, a vent port and a drain port molded into the base of the eye piece. The fill, drain and vent ports are designed and sized for fast fill to minimize the patient's time with their eye immersed in the saline solution; for venting of any bubbles that may form, for example, if the seal on the patient's head leaks or the patient pulls away from the machine; and for rapid draining of the saline solution back into a plastic saline bag after scanning is completed. An RF Identification chip may be molded into the plastic base of the eye piece or, alternately into the conformable face seal of the eye piece. This RF ID chip can communicate with an RF pick-up device located on or inside the scanning machine body. The RF ID chip can transfer information to the RF pick-up device to identify the specific patient associated with the eye piece and to record, for example, how many scans the patient has undergone using that eye piece.

The components of a disposable eye piece system form an integrated disposable package that can be assembled, packaged, transported and used while maintaining the eye piece and saline solution in an sterile condition by applying aseptic techniques at each stage of the assembly, packaging, shipping, storage and scanning process. The above procedure can provide an eye piece, associated tubing internal diameters and saline solution as a system closed to ambient air from assembly through applying the eye seal to a patient immediately prior to scanning.

This closed system approach may include a protective container positioned over the eye seal during packaging to protect the eye piece from distorting or damage during handling, shipping and storage. The protective container can also be used for handling the eyepiece by the scanning physician or technician while the disposable package is removed from its shipping box and the eye piece is installed onto the scanning machine body. The side of the eye piece that conforms to the patient's face is the face seal portion of the eye piece. The side of the eye piece that engages the instrument body of the scanning device using attaching mechanisms is the instrument engagement portion of the eye piece. The fill and vent ports are on the top or first end of the eye piece and the drain port is on the bottom or second end of the eye piece.

The disposables package may also include several sterile wipes for use on the headrest cushions that may be optionally attached to the scanning machine body. All of the disposable components can be packaged in a sealed plastic bag by aseptic techniques and the bag further packaged, for example, in an appropriately labeled cardboard box.

The protective shipping container disclosed above 1) protects the eye piece from damage, human contact and exposure to ambient air during shipping and storage and 2) allows the scanning physician or technician to attach the eye piece to the scanning machine and prepare the eye piece for the patient without compromising the sterile condition of the eye piece.

One embodiment of the present disclosure is an eyepiece for an ultrasonic scanning device, comprising a base having a face seal portion, the face seal portion defining a partially enclosed volume, the face seal portion having a first end and a second end disposed opposite of the first end; a fill port disposed proximate to the first end of the face seal portion, the fill port providing fluid communication between the partially enclosed volume and an ambient environment; a vent port disposed proximate to the first end of the face seal portion, the vent port providing fluid communication between the partially enclosed volume and the ambient environment; and a drain port disposed proximate to the second end of the face seal portion, the drain port providing fluid communication between the partially enclosed volume and the ambient environment.

Another embodiment of the present disclosure is a method of producing an eyepiece for an ultrasonic scanning device, comprising providing a base having a face seal portion, the face seal portion defining a partially enclosed volume, the face seal portion having a first end and a second end disposed opposite of the first end; providing a fill port on the face seal portion proximate to the first end of the face seal portion, the fill port providing fluid communication between the partially enclosed volume and an ambient environment; providing a vent port on the face seal portion proximate to the first end of the face seal portion, the vent port providing fluid communication between the partially enclosed volume and the ambient environment; and providing a drain port on the face seal portion proximate to the second end of the face seal portion, the drain port providing fluid communication between the partially enclosed volume and the ambient environment.

Yet another embodiment of the present disclosure is a system for protecting an eyepiece for an ultrasonic scanning device, comprising a protective container comprising a top piece selectively interconnected to a bottom piece, the protective container defining an enclosed volume, an eyepiece comprising a base having a face seal portion, the face seal portion defining a partially enclosed volume, the face seal portion having a first end and a second end disposed opposite of the first end; a fill port, a vent port, and a drain port disposed on the face seal portion, the fill port, the vent port, and the drain port providing fluid communication between the partially enclosed volume and an ambient environment; and wherein the eyepiece is disposed in the enclosed volume formed by the top piece and the bottom piece of the protective container.

Yet another embodiment of the present disclosure is a package comprising an eye piece for ultrasound imaging of an ocular feature of a patient, a length of tubing for at least one of filling a portion of the eye piece with a saline solution, draining saline solution from the portion of the eye piece, and venting air from the portion of the eye piece and a disposable container closed from ambient air and comprising the eye piece, the length of tubing, and a sterile saline solution to maintain the eye piece and length of tubing in the sterile saline solution prior to use by a patient.

Yet another embodiment of the present disclosure is a device comprising an eye piece for use in imaging an ocular feature of a patient wherein the eye piece is comprised of a face seal portion and an instrument engagement portion and a protective container engaged with and/or containing the eye piece, wherein the protective container is removably attached to the eye piece to enable a user to attach the instrument engagement portion of the eye piece to a scanning machine prior to removal of the protective container from face seal portion of the eye piece.

Yet another embodiment of the present disclosure is a method, comprising providing an eye piece for use in imaging an ocular feature of a patient and a protective container engaged with and/or containing the eye piece wherein the protective container comprises a first part protecting the face seal portion of the eye piece and a second part covering the instrument engagement portion of the eye piece, disengaging, by a user, the second part of the protective container, wherein after disengaging, the first part remains engaged with the eye piece while the second part does not, engaging, by a user, the instrument engagement portion of the eye piece with a scanning machine, wherein the first part and eye piece do not move independently during engaging and wherein during engaging the user grasps the first part and disengaging the first part from the eye piece after the eye piece is engaged with the scanning machine.

The following definitions are used herein:

The phrases at least one, one or more, and and/or are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together.

An acoustically reflective surface or interface is a surface or interface that has sufficient acoustic impedance difference across the interface to cause a measurable reflected acoustic signal. A specular surface is typically a very strong acoustically reflective surface.

Anterior means situated at the front part of a structure; anterior is the opposite of posterior.

An A-scan is a representation of a rectified, filtered reflected acoustic signal as a function of time, received by an ultrasonic transducer from acoustic pulses originally emitted by the ultrasonic transducer from a known fixed position relative to an eye component.

An accommodative lens, also known as a presbyopic lens or presby lens, is an artificial intraocular lens that changes its focal distance in response to contraction of the ciliary body. When successfully implanted, an accommodative lens reverses presbyopia, the inability of the eye to change its focal distance from far to near.

Accuracy as used herein means substantially free from measurement error.

Aligning means positioning the acoustic transducer accurately and reproducibly in all three dimensions of space with respect to a feature of the eye component of interest (such as the center of the pupil, center of curvature or boundary of the cornea, lens, retina, etcetera).

The anterior chamber comprises the region of the eye from the cornea to the iris.

The anterior segment comprises the region of the eye from the cornea to the back of the lens.

An precision ultrasonic scanner is an ultrasound scanning device utilizing a transducer that both sends and receives pulses as it moves along 1) an arcuate guide track, which guide track has a center of curvature whose position can be moved to scan different curved surfaces; 2) a linear guide track; and 3) a combination of linear and arcuate guide tracks which can create a range of centers of curvature whose position can be moved to scan different curved surfaces.

Automatic refers to any process or operation done without material human input when the process or operation is performed. However, a process or operation can be automatic, even though performance of the process or operation uses material or immaterial human input, if the input is received before performance of the process or operation. Human input is deemed to be material if such input influences how the process or operation will be performed. Human input that consents to the performance of the process or operation is not deemed to be "material."

Auto-centering means automatically, typically under computer control, causing centration of the arc scanning transducer with the eye component of interest.

A B-scan is a processed representation of A-scan data by either or both of converting it from a time to a distance using acoustic velocities and by using grayscales, which correspond to A-scan amplitudes, to highlight the features along the A-scan time history trace (the latter also referred to as an A-scan vector).

A canthus is the angular junction of the eyelids at either corner of the eye where the upper and lower eyelids meet.

Center of rotation of the eye, there is a point within the eyeball that is more or less fixed relative to the orbit when the eye rotates in its orbit. It is considered that the center of rotation of an emmetropic eye (that is, a normal eye with about 20/20 vision) lies on the line of sight of the eye about 13.5 mm behind the anterior pole of the cornea when the line of sight of the eye is perpendicular to both the base line and the frontal plane.

Centration means substantially aligning the center of curvature of a precision arc scanning transducer in all three dimensions of space with the center of curvature of the eye component of interest (such as the cornea, pupil, lens, retina, etcetera) such that rays from the transducer pass through both centers of curvature. A special case is when both centers of curvature are coincident.

The ciliary body is the circumferential tissue inside the eye composed of the ciliary muscle and ciliary processes. There are three sets of ciliary muscles in the eye, the longitudinal, radial, and circular muscles. They are near the front of the eye, above and below the lens. They are attached to the lens by connective tissue called the zonule of Zinn, and are responsible for shaping the lens to focus light on the retina. When the ciliary muscle relaxes, it flattens the lens, generally improving the focus for farther objects. When it contracts, the lens becomes more convex, generally improving the focus for closer objects.

Coronal means of or relating to the frontal plane that passes through the long axis of a body. With respect to the eye or the lens, this would be the equatorial plane of the lens which also approximately passes through the nasal canthus and temporal canthus of the eye.

Eye Piece as used herein means the eye piece assembly comprised of a body which is further comprised of a clamp and a membrane, and a seal which seals the eye piece to the patient.

Fiducial means a reference, marker or datum in the field of view of an imaging device.

Fixation means having the patient focus an eye on an optical target such that the eye's optical axis is in a known spatial relationship with the optical target. In fixation, the light source is axially aligned in the arc plane with the light source in the center of the arc so as to obtain maximum signal strength such that moving away from the center of the arc in either direction results in signal strength diminishing equally in either direction away from the center.

A guide is an apparatus for directing the motion of another apparatus.

Haptics are little protrusions extending from the outer diameter of some types of artificial lenses. These haptics fix the position of the lens to the ciliary body by protruding into the ciliary sulcus. In the case of accommodative lenses, the haptics enable the lens to accommodate in response to the action of the ciliary body.

The home position of a precision imaging ultrasound transducer is its position during the registration process.

An imaging ultrasound transducer is the device that is responsible for creating the outgoing ultrasound pulse and detecting the reflected ultrasound signal that is used for creating the A-Scans and B-Scans.

An intraocular lens is an artificial lens that is implanted in the eye to take the place of the natural lens.

LASIK is a procedure performed on the cornea for correcting refractive errors, such as myopia, hyperopia, and astigmatism. Commonly, an excimer laser selectively removes tissue from the inside of the cornea, after it is exposed, by cutting a thin flap, so as to reshape the external shape of the cornea.

As used herein, a meridian is a 2-dimensional plane section through the approximate center of a 3-dimensional eye and its angle is commonly expressed relative to a horizon defined by the nasal canthus and temporal canthus of the eye.

The natural lens (also known as the aquula or crystalline lens) is a transparent, biconvex structure in the eye that, along with the cornea, helps to refract light to be focused on the retina. The lens, by changing shape, functions to change the focal distance of the eye so that it can focus on objects at various distances, thus allowing a sharp real image of the object of interest to be formed on the retina. This adjustment of the lens is known as accommodation. The lens is located in the anterior segment of the eye behind the iris. The lens is suspended in place by the zonular fibers, which attach to the lens near its equatorial line and connect the lens to the ciliary body. The lens has an ellipsoid, biconvex shape whose size and shape can change due to accommodation and due to growth during aging. The lens is comprised of three main parts: namely the lens capsule, the lens epithelium, and the lens fibers. The lens capsule forms the outermost layer of the lens and the lens fibers form the bulk of the interior of the lens. The cells of the lens epithelium, located between the lens capsule and the outermost layer of lens fibers, are generally found only on the anterior side of the lens.

Ocular means having to do with the eye or eyeball.

Ophthalmology means the branch of medicine that deals with the eye.

Optical as used herein refers to processes that use light rays.

The optical axis of the eye is a straight line through the centers of curvature of the refracting surfaces of an eye (the anterior and posterior surfaces of the cornea and lens).

As used herein, the orbit of the eye is the cavity or socket of the skull in which the eye and its appendages are situated. In the adult human, the volume of the orbit is about 30 ml, of which the eye occupies about 6.5 ml.

Pachymetry or corneal pachymetery is technically referred to as Time Domain Reflectometry ultrasound. A pulse of ultrasonic energy is sent toward the cornea and the time spacing of the returning echoes are used to arrive at corneal thickness.

Phakic intraocular lenses, or phakic lenses, are lenses made of plastic or silicone that are implanted into the eye permanently to reduce a person's need for glasses or contact lenses. Phakic refers to the fact that the lens is implanted into the eye without removing the eye's natural lens. During phakic lens implantation surgery, a small incision is normally made in the front of the eye. The phakic lens is inserted through the incision and placed just in front of or just behind the iris.

Positioner means the mechanism that positions a scan head relative to a selected part of an eye. In the present disclosure, the positioner can move back and forth along the x, y or z axes and rotate in the β direction about the z-axis. Normally the positioner does not move during a scan, only the scan head moves. In certain operations, such as measuring the thickness of a region, the positioner may move during a scan.

Position tracking sensors are a set of position sensors whose sole purpose is to monitor the movement of the eye or any other anatomical feature during the imaging scan so as to remove unwanted movement of the feature when forming a scanned image.

Posterior means situated at the back part of a structure; posterior is the opposite of anterior.

The posterior chamber comprises the region of the eye from the back of the iris to the front of the lens.

The posterior segment comprises the region of the eye from the back of the lens to the rear of the eye comprising the retina and optical nerve.

Precise as used herein means sharply defined and repeatable.

Precision means how close in value successive measurements fall when attempting to repeat the same measurement between two detectable features in the image field. In a normal distribution precision is characterized by the standard deviation of the set of repeated measurements. Precision is very similar to the definition of repeatability.

Presbyiopia is typically caused by a loss of elasticity of the natural lens inside the eye. This occurs as part of the ageing process and, although it cannot be 'cured', it can be corrected by wearing glasses or implanting an artificial lens.

The pulse transit time across a region of the eye is the time it takes a sound pulse to traverse the region.

Purkinje images are reflections of objects from structure of the eye. There are at least four Purkinje images that are visible on looking at an eye. The first Purkinje image (P1) is the reflection from the outer surface of the cornea. The second Purkinje image (P2) is the reflection from the inner surface of the cornea. The third Purkinje image (P3) is the reflection from the outer (anterior) surface of the lens. The fourth Purkinje image (P4) is the reflection from the inner (posterior) surface of the lens. Unlike the others, P4 is an inverted image. The first and fourth Purkinje images are used by some eye trackers, devices to measure the position of an eye. Purkinje images are named after Czech anatomist Jan Evangelista Purkyně (1787-1869).

Refractive means anything pertaining to the focusing of light rays by the various components of the eye, principally the cornea and lens.

Registration as used herein means aligning.

Saccades are quick, simultaneous rotations of both eyes in the same direction involving a succession of discontinuous individual rotations of the eye orbit in the eye socket. These rapid motions can be on the order of 20 degrees of rotation with a maximum velocity of 200 degrees/sec and are a part of normal eyesight.

Scan head means the mechanism that comprises the ultrasound transducer, the transducer holder and carriage as well as any guide tracks that allow the transducer to be moved relative to the positioner. Guide tracks may be linear, arcuate or any other appropriate geometry. The guide tracks may be rigid or flexible. Normally, only the scan head is moved during a scan.

Sector scanner is an ultrasonic scanner that sweeps a sector like a radar. The swept area is pie-shaped with its central point typically located near the face of the ultrasound transducer.

A specular surface means a mirror-like surface that reflects either optical or acoustic waves. For example, an ultrasound beam emanating from a transducer will be reflected directly back to that transducer when the beam is aligned perpendicularly to a specular surface.

The ciliary sulcus is the groove between the iris and ciliary body. The scleral sulcus is a slight groove at the junction of the sclera and cornea.

The suprachoroid lies between the choroid and the sclera and is composed of closely packed layers of long pigmented processes derived from each tissue.

The suprachoroidal space is a potential space providing a pathway for uveoscleral outflow and becomes an actual space in choroidal detachment. The hydrostatic pressure in the suprachoroidal space is an important parameter for understanding intraocular fluid dynamics and the mechanism of choroidal detachment.

Tissue means an aggregate of cells usually of a particular kind together with their intercellular substance that form one of the structural materials of a plant or an animal and that in animals include connective tissue, epithelium, muscle tissue, and nerve tissue.

A track or guide track is an apparatus along which another apparatus moves. In an ultrasound scanner or combined ultrasound and optical scanner, a guide track is an apparatus along which one or more ultrasound transducers and/or optical probes moves during a scan.

Ultrasound Bio Microscopy (UBM) is an imaging technique using hand-held ultrasound device that can capture anterior segment images using a transducer to emit short acoustic pulses ranging from about 20 to about 80 MHz. This type of ultrasound scanner is also called a sector scanner. The UBM method is capable of making qualitative ultrasound images of the anterior segment of the eye but cannot unambiguously make accurate, precision, comprehensive, measurable images of the cornea, lens or other components of the eye.

Ultrasonic means sound that is above the human ear's upper frequency limit. When used for imaging an object like the eye, the sound passes through a liquid medium, and its frequency is many orders of magnitude greater than can be detected by the human ear. For high-resolution acoustic imaging in the eye, the frequency is typically in the approximate range of about 5 to about 80 MHz.

A vector refers to a single acoustic pulse and its multiple reflections from various eye components. An A-scan is a representation of this data whose amplitude is typically rectified.

The visual axis of the eye is the line joining the object of interest and the fovea and which passes through the nodal points of the eye.

Zonules are tensionable ligaments extending from near the outer diameter of the crystalline lens. The zonules attach the lens to the ciliary body which allows the lens to accommodate in response to the action of the ciliary muscle.

BRIEF DESCRIPTION OF THE DRAWINGS

The present invention may take form in various components and arrangements of components, and in various steps and arrangements of steps. The drawings are only for purposes of illustrating the preferred embodiments and are not to be construed as limiting the invention. In the drawings, like reference numerals may refer to like or analogous components throughout the several views.

FIG. 8b illustrates is a detailed view of the tongue and groove connection of FIG. 8a;

DETAILED DESCRIPTION OF THE DRAWINGS

Figure 1A:
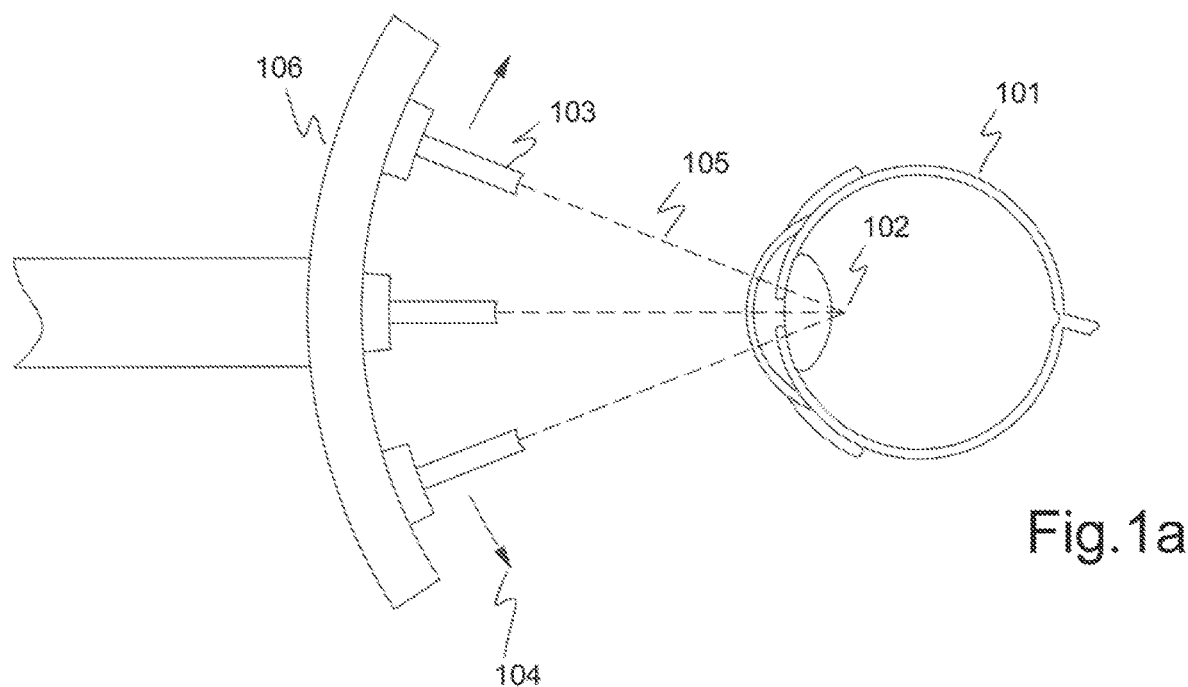
FIG. 1a illustrates a first type of scanning strategy for ultrasonic scanners.

The main elements of a human eye are shown, for example, in "Optics of the Human Eye", D. A. Atchison, G. Smith, Robert Stevenson House, Edinburgh, ISBN 0 7506 3775 7, first printed in 2000. The cornea, which is optically transparent, is located at the front of the eye and is located in the anterior chamber. The anterior and posterior surfaces of a normal cornea and the internal layers, such as Bowman's layer, within a normal cornea are specular surfaces. The iris separates the anterior chamber from the posterior chamber. The back of the lens forms the rear of the posterior chamber. The natural lens sits directly behind the iris. Only the central part of the lens, which is behind the pupil, can be seen optically. The anterior and posterior surfaces of a normal lens are specular surfaces. The cornea, iris and lens comprise the main optical refractive components of the eye. The anterior and posterior chambers comprise the anterior segment of the eye. The main volume or posterior segment of the eye lies behind the lens, with the retina and optical nerve at the rear of the posterior segment of the eye. The composition of the eye's aqueous and vitreous humor are very close to that of water with a density of about 1,000 kg/m$^3$, and this allows the eye to be a suitable medium for the transmission of acoustic energy.

The optical axis is the line passing through the centers of curvature of the cornea and lens assuming they are centered as they are in a normal eye. The visual axis is the line joining the fixation point and the fovea which is in the retina.

Optical means are suitable for viewing the anterior chamber and for viewing near the entire central axis of the eye. However, under normal conditions, optical means cannot be used to view the portions of the posterior chamber lying far off-axis and behind the iris because light does not penetrate the iris. These portions include the suspensory ligaments (also known as zonules), the sulcus and the ciliary body. However, the eye components that cannot be viewed optically, can be viewed with suitably high-frequency acoustic energy because high-frequency acoustic energy can readily penetrate the iris. As is well-known, acoustic frequencies in the ultrasonic range of about 5 MHz to about 100 MHz can be used to provide very high resolution images of, for example, the cornea and the lens. The basics of ultrasonic scanning for the eye are described in "Ultrasonography of the Eye and Orbit", Second Edition, Coleman et al, published by Lippincott Williams & Wilkins, 2006. Also, optical means have difficulty measuring the region between the cornea and iris and cannot image stents that are placed near the suprachoroidal space to help relieve the symptoms of glaucoma.

A typical focused ultrasonic transducer has an aperture which is slightly concave with a radius of curvature that focuses the acoustic pulses at a desired location. For the example of a transducer with a diameter of 5 mm, a focal length of 15 mm, a center frequency of about 38 MHz, the depth of focus is about 1,560 microns.

As can be appreciated, an ultrasound transducer with a concave aperture is preferred. In precision scanning of an eye feature of interest, it is typically preferred to place the focal plane of the ultrasound transducer as close to the feature of interest as possible. Obtaining a strong, sharp image of an eye feature of interest involves fulfilling at least 2 conditions: (1) the focal plane must be located near the feature of interest and (2) the transducer pulse must engage the surface of interest substantially perpendicular to the surface of the feature of interest. This latter condition can be fulfilled in a precision arc scanning device if the pulse wave train passes through both the center of curvature of the transducer arcuate track guide and the center of curvature of the eye component surface.

Precision ultrasound arc scanning machines have demonstrated that they can repeatedly produce an image of eye features as small as about 2 to 5 microns in the depth direction (z-direction) and about 50 microns in either lateral direction (x- and y-directions). For example, scans of a cornea can image the epithelial layer, Bowman's layer and, if present, LASIK flap scars, all in a cornea that is about 500 microns thick. Thus it is important to be able to account for any unintended motions of the patient's head or eye during a scan, especially if multiple scans are made and later spliced together to form a composite image. Such a method of tracking is disclosed in US Publication No. 2013/0,310,692, which is herein incorporated by reference in its entirety.

FIG. 1 illustrates two different types of scanning strategies for ultrasonic scanners capable of imaging most regions of the interior of an eye. FIG. 1a illustrates the arc scanning principle for producing an ultrasonic scan of a component of an eye 101. In this type of scanner, which is described, for example, in U.S. Pat. Nos. 6,315,727, 6,491,637, 6,887,203 and 7,048,690, which are herein incorporated by reference in their entirety, a transducer is moved in an arc whose center is set at a location of interest 102 in the eye. In FIG. 1a, an ultrasonic transducer is shown in a sequence of positions such as positions 103 and 104 with the center of the arc at approximately the center of curvature of the cornea. The transducer is moved in an arc as shown to produce many A-scans along the arc which can then be combined to form a B-scan which is a cross-sectional image of the eye features of interest.

Figure 1B:
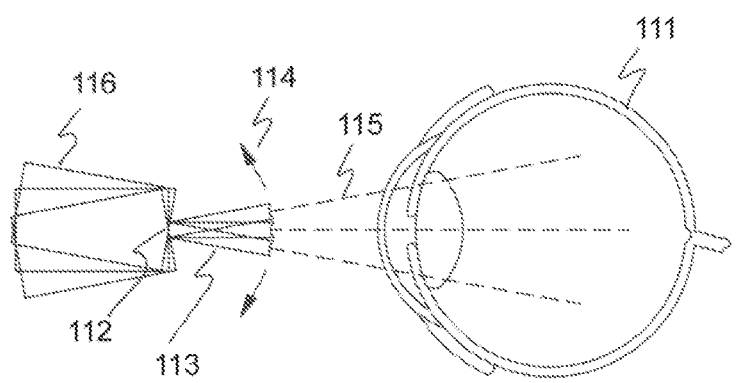
FIG. 1b illustrates a second type of scanning strategy for ultrasonic scanner.

FIG. 1b illustrates the sector scanning principle for producing an ultrasonic image of a particular location with an eye 111. In this type of scanner, which is described, for example, in U.S. Pat. Nos. 4,245,250, 4,817,432, 5,029,587 and 5,331,962, an ultrasonic transducer is shown being rotated about a fixed position 112 so as to produce an image in a localized region of interest within the eye. The scanning method illustrated in this figure is called sector scanning.

In both the arc and sector ultrasonic scanners, the transducer acts as both the transmitter and receiver of acoustic signals. This technique is described, for example, in U.S. Pat. No. 5,293,871, which is herein incorporated by reference in its entirety. The transducer emits a short acoustic pulse and then receives the reflected acoustic signal.

A sector scanner can be used to measure the thickness of an eye component such as, for example, the thickness of the cornea or the thickness of the lens. A sector scanner cannot be used to measure the breadth of specular features that extend laterally, such as, for example, the length of a LASIK scar, because only that small portion of the cornea that is perpendicular to the acoustic beam and reflects acoustic energy back to the transducer is visible to a sector scanner.

An arc scanner, on the other hand, can be used to measure the thickness of an eye component such as, for example, the thickness of the cornea or the thickness of a lens as well as to measure the length of specular features that extend laterally, such as, for example, the length of a LASIK scar or the lateral length of a natural or implanted lens.

Figure 2:
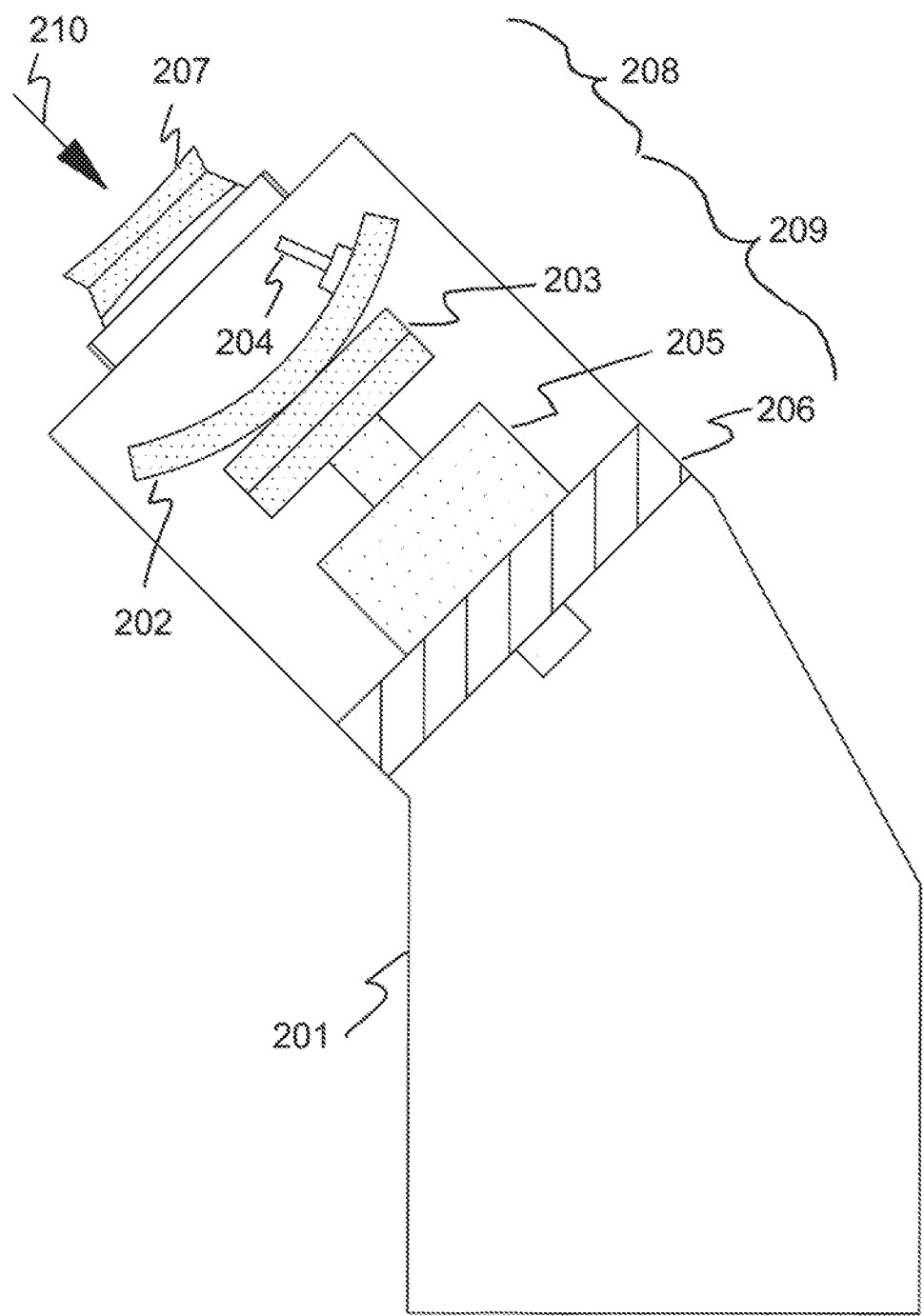
FIG. 2 is a schematic of the principal elements of a prior art ultrasound eye scanning device which is prior art.

FIG. 2 is a schematic of the principal elements of a prior art ultrasound eye scanning device such as described in U.S. Pat. No. 8,317,709. The scanning apparatus 201 of this example is comprised of a scan head assembly 208, shown here as an arcuate guide 202 with scanning transducer 204 on a transducer carriage which moves back and forth along the arcuate guide track, and a linear guide track 203 which moves the arcuate guide track back and forth as described in FIG. 5; a positioning mechanism 209 comprised of an x-y-z and beta mechanisms 205 as described in FIG. 4 mounted on a base 206 which is rigidly attached to scanning apparatus 201; and a disposable eyepiece 207. The scanning device 201 is typically connected to a computer (not shown) which includes a processor module, a memory module, and a video monitor. The patient is seated at the device 201 with their eye engaged with disposable eyepiece 207. The patient is typically looking downward during a scan sequence. The patient is fixed with respect to the scanning device 201 by a headrest system such as shown in FIG. 6 and by the eyepiece 207. The operator using, for example, a mouse and/or a keyboard and video screen inputs information into the computer selecting the type of scan and scan configurations as well as the desired type of output analyses. The operator, for example, again using a mouse and/or a keyboard, a video camera located in the scanning machine and video screen, then centers a reference marker such as, for example, a set of cross hairs displayed on a video screen on the desired component of the patient's eye which is also displayed on video screen. This is done by setting one of the cross hairs as the prime meridian for scanning. These steps are carried out using the positioning mechanism which can move the scan head in the x, x, z and beta space (three translational motions plus rotation about the z-axis). Once this is accomplished, the operator instructs computer using either a mouse and/or a keyboard to proceed with the precision scanning sequence. Now the computer processor takes over the procedure and issues instructions to the scan head 208 and the transducer 204 and receives positional and imaging data. The computer processor proceeds with a sequence of operations such as, for example: (1) with the transducer carriage substantially centered on the arcuate guide track, rough focusing of transducer 204 on a selected eye component; (2) accurately centering of the arcuate guide track with respect to the selected eye component; (3) accurately focusing transducer 204 on the selected feature of the selected eye component; (4) rotating the scan head through a substantial angle (including orthogonal) and repeating steps (1) through (3) on a second meridian; (5) rotating the scan head back to the prime meridian; (6) initiating a set of A-scans along each of the of selected scan meridians, storing this information in the memory module; (7) utilizing the processor, converting the A-scans for each meridian into a set of B-scans and then processing the B-scans to form an image associated with each meridian; (8) performing the selected analyses on the A-scans, B-scans and images associated with each or all of the meridians scanned; and (9) outputting the data in a preselected format to an output device such as a printer. As can be appreciated, the patient's head must remain fixed with respect to the scanning machine 201 during the above operations when scanning is being carried out, which in a modern precision ultrasound scanning machine, can take several seconds.

An eyepiece serves to complete a continuous acoustic path for ultrasonic scanning, that path extending in water from the transducer to the surface of the patient's eye. The eyepiece 207 also separates the water in which the patient's eye is immersed from the water in the chamber in which the transducer guide track assemblies are immersed. The patient sits at the machine and looks down through the eyepiece 207 as shown by arrow 210. Finally, the eyepiece provides an additional steady rest for the patient and helps the patient to remain steady during a scan procedure.

Figure 3:
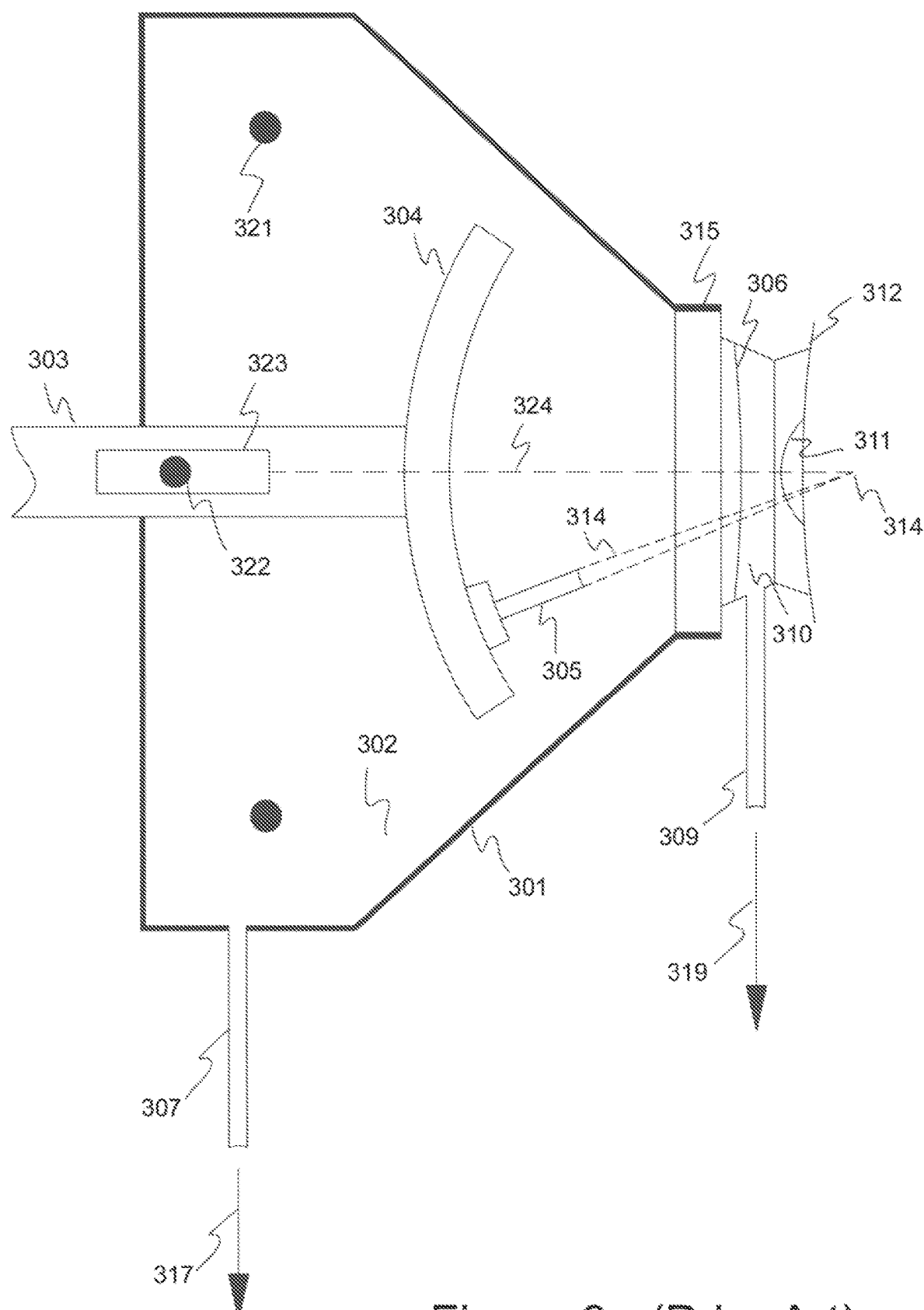
FIG. 3 is a schematic of a prior art precision arc scanning device.

FIG. 3 shows the main elements of a precision arc scanning device illustrating positioning of a transducer along an arcuate guide track whose center of curvature is centered approximately on the center of curvature of an eye component of interest. FIG. 3 shows fixation target lights 321 and 322 that allow the patient to fixate his or her eye to maintain it in a steady eye position during scanning FIG. 3 also shows an optical video camera 323 which may be used by the operator of the arc scanner to monitor the position of the patient's eye and to determine whether the patient's eye is open before a scan is initiated. The transducer and its arcuate guide assembly are immersed in a chamber of water 302 to provide a transmission path for the acoustic signals. The patient's eye must also be immersed in water to provide continuity of the transmission path for the acoustic signal.

FIG. 3 also shows a hygienic barrier 306 which separates the water chamber 301 in which the transducer 305 and arc guide assembly 304 are contained from the water 310 in which the patient's eye is immersed. This barrier 306 provides the separation of water 302 in which the transducer 305 and arc track assembly 304 are immersed from the water 310 in which the patient's eye is immersed. The arcuate guide assembly and associated components may be contaminated, for example, by particles from wearing mechanical components. The water 310 in which the patients eye is immersed may be contaminated by bacteria or virus particles from the patient. As can be appreciated, the water 310 in which the patients eye is immersed should be changed for every patient to prevent possible disease transmission. As can be further appreciated, the hygienic membrane 306 must be substantially transparent to ultrasound so as to maintain a clear acoustic transmission path between the patient's eye and the ultrasonic transducer. The hygienic membrane 306 is typically formed as part of a disposable eyepiece such as described in FIGS. 7 through 11.

The transmission path for acoustic energy is thus from the transducer through the water bath within the scanner body, through the membrane; through the water or saline solution in the eye piece; and into the patient's eye. The water, saline solution, membrane and patient's eye fluids all have substantially the same acoustic impedance.

References are made herein to a medium suitable for conducting acoustic energy in the form of ultrasound. There are reasons to prefer that the medium be pure water or physiologic saline (also known as normal saline) but the embodiments do not exclude other media suitable for conducting acoustic energy in the form of ultrasound. Most other media present an increased danger to the patient's eye, even with a barrier interposed between the eye and the ultrasound transducer. Barriers can leak or be breached, allowing the liquids on either side to mix, thus bringing a potentially harmful material into contact with the eye.

It should be appreciated, however, that non-harmful, less-corrosive media and leakproof, impenetrable barriers might be developed or discovered. This might allow different media than pure water or physiologic saline to be used in this invention. Nothing about embodiments herein other than the hazards just described requires pure water or physiologic saline to be present in the chamber containing the transducer. All references to water in the following should accordingly be understood as referring to any suitable liquid.

FIG. 3 illustrates the continuity of an acoustic transmission path through water. A chamber 301 of water 302 is shown with a positioning arm 303 and arc guide assembly 304 on which an ultrasonic transducer 305 is mounted. An ultrasonically transparent barrier 306 separates chamber 301 from the interior of an eyepiece. The eyepiece contains a separate volume of water 310 which fills the interior of the eyepiece and contacts a patient's eye surface 311. The eyepiece is connected and sealed to the main chamber 301 of the arc scanning device, and is also sealed against the patient's face 312. As can be seen, there is a continuous path through water from the transducer 305 to the patient's eye surface 311 for the efficient passage of acoustic energy. The barrier 306 readily passes acoustic energy without alteration, thus forming a portion of the continuous path between the transducer 305 and the patient's eye surface 311. Since the acoustic impedance of the patient's eye is approximately that of water, the acoustic energy from the transducer can be efficiently transmitted into the eye and reflected back from an eye component, such as for example, the surface of the cornea, to the transducer. Also shown in FIG. 3 are a water fill tube 307 for the main chamber 301 and a separate water fill tube 309 for the eyepiece.

As can be appreciated, the water used in the eyepiece can be distilled or physiologic saline to match the salinity of the eye, and the water used in the eyepiece can be introduced at a temperature that is comfortable for the patient. The water used in the main chamber 301 eyepiece is preferably distilled to minimize build-up of precipitates on the moving parts in the chamber over time.

Figure 4:
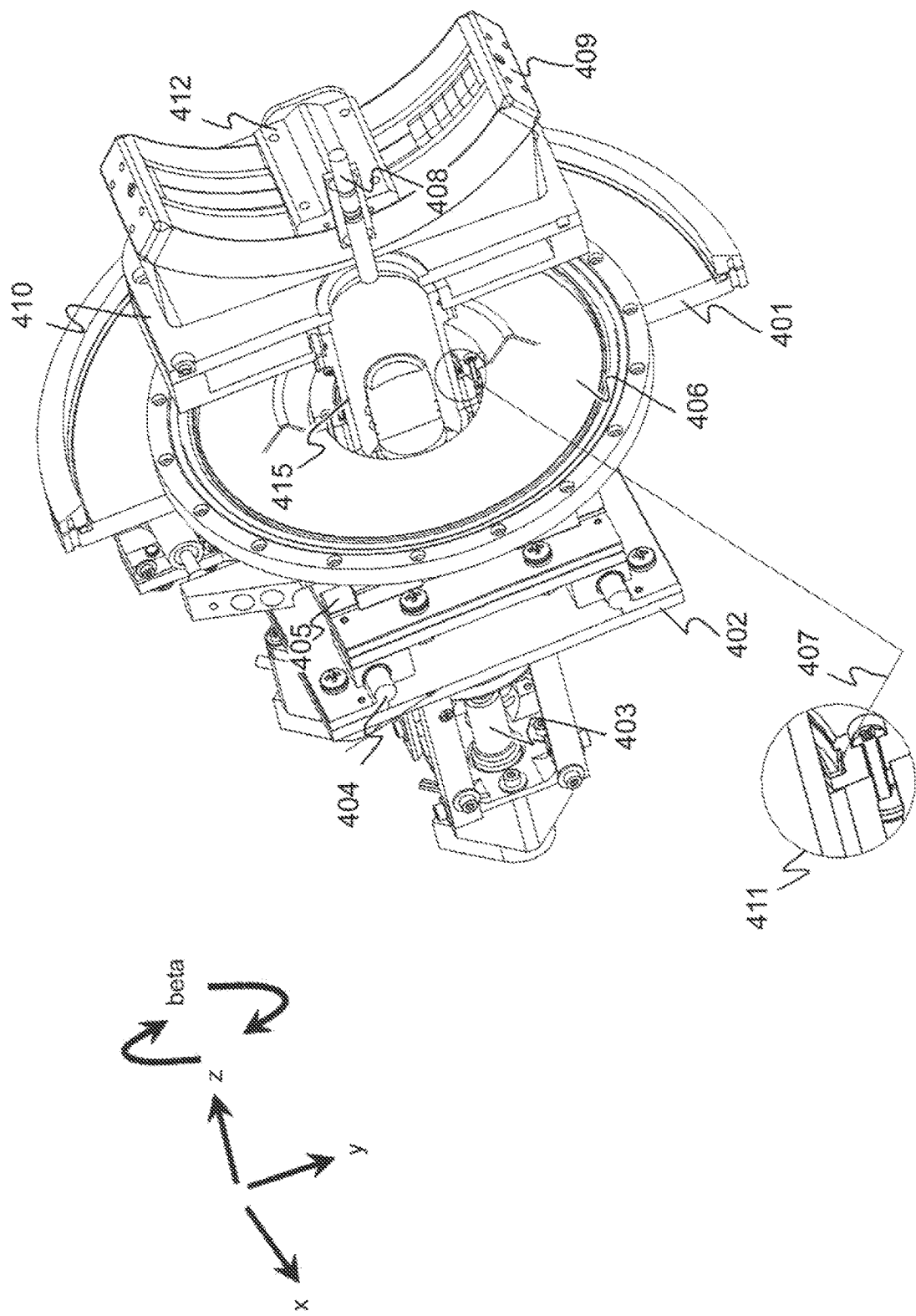
FIG. 4 illustrates a prior art arc scanning head positioning mechanism.

FIG. 4 illustrates a prior art compact arc scan head and scan head positioning mechanism which has been disclosed previously in U.S. Pat. No. 8,758,252 "Components for an Ultrasonic Arc Scanning Apparatus," which is herein incorporated by reference in its entirety. FIG. 4 shows a scan head assembly comprised of scan head mount structure 410 and a scan head assembly comprising an arcuate guide track 409 with an ultrasound transducer 408 mounted on transducer carriage 412. Transducer carriage 412 may be moved back and forth along arcuate guide track 409 to perform an arc scan. The scan head assembly is attached to a main positioner arm 415 (shown in a sectional view). The scan head mount structure 410, arcuate track 409, transducer carriage 412 and scanning transducer 408 are operative under water and are sealed from the rear portion of the positioning mechanism by a translational seal 406 and a rotational seal 407. The translational seal 406 is typically formed by a large rubber membrane that can flex with the small x and y motions required by the scanning head positioner, although alternate sealing mechanisms may be employed. The z-axis seal and rotational seal 407 seal against the main positioner arm 415 which can both rotate and move in and out in the z-direction. Translational seal 406 is attached to stationary plate 401 which, in turn, is affixed to the main arc scanner water tank (not shown) which, in turn, is fixed with respect to the patient being scanned. The z-axis and rotational seal 407, which is shown in close-up view 411, is typically formed by a circumferential groove type sealing mechanism with the groove facing into the water, although alternate sealing mechanisms may be employed. Available seals allow both rotation and axial translation of the center tube while maintaining a water tight seal. Plate 402 forms a platform for the x- and y-positioning mechanisms. Plate 402 is fixed relative to stationary plate 401. The scanning head assembly can be moved back and forth axially (the z-direction) by axial piston 403 or another suitable mechanism. The scanning head assembly can be rotated (the beta-direction) about the z-axis by a rotary stepping motor (not shown) or another suitable device. The scanning head assembly can be moved up and down (the y-direction) by piston 405 or another suitable mechanism. The scanning head assembly can be moved from side to side (the x-direction) by piston 404 or another suitable mechanism. The components to the left or rear of stationary plate 401 remain in ambient air while the components to the right or front of stationary plate 401 are in immersed in water when the arc scanner is operational.

Typically, the scan head assembly is moved in the x-, y-, z- and beta directions by the scan head positioning mechanism to position the scan head assembly with respect to an eye component of interest. Although these motions are typically made rapidly under computer control, scans of the eye are typically not made during positioning. Once the scan head assembly is positioned with respect to the eye component of interest, scans are made by the transducer carriage 412 moving back and forth along the arcuate guide track 409 on the scan head. As described in U.S. Pat. No. 8,758,252, the transducer carriage 412 moves along arcuate guide track 409 on a fluid bearing for smooth operation.

As described above, the scan head can be moved by the scan head positioning mechanism back and forth axially (the z-direction); rotated (the beta-direction) about the z-axis; moved up and down (the y-direction); and moved from side to side (the x-direction). It is therefore possible to move the entire scan head in more complex motions by coordinating these movements to obtain scans that cannot be obtained by a simple arc scan. A scan head of a more advanced device is illustrated in FIG. 5.

Figure 5:
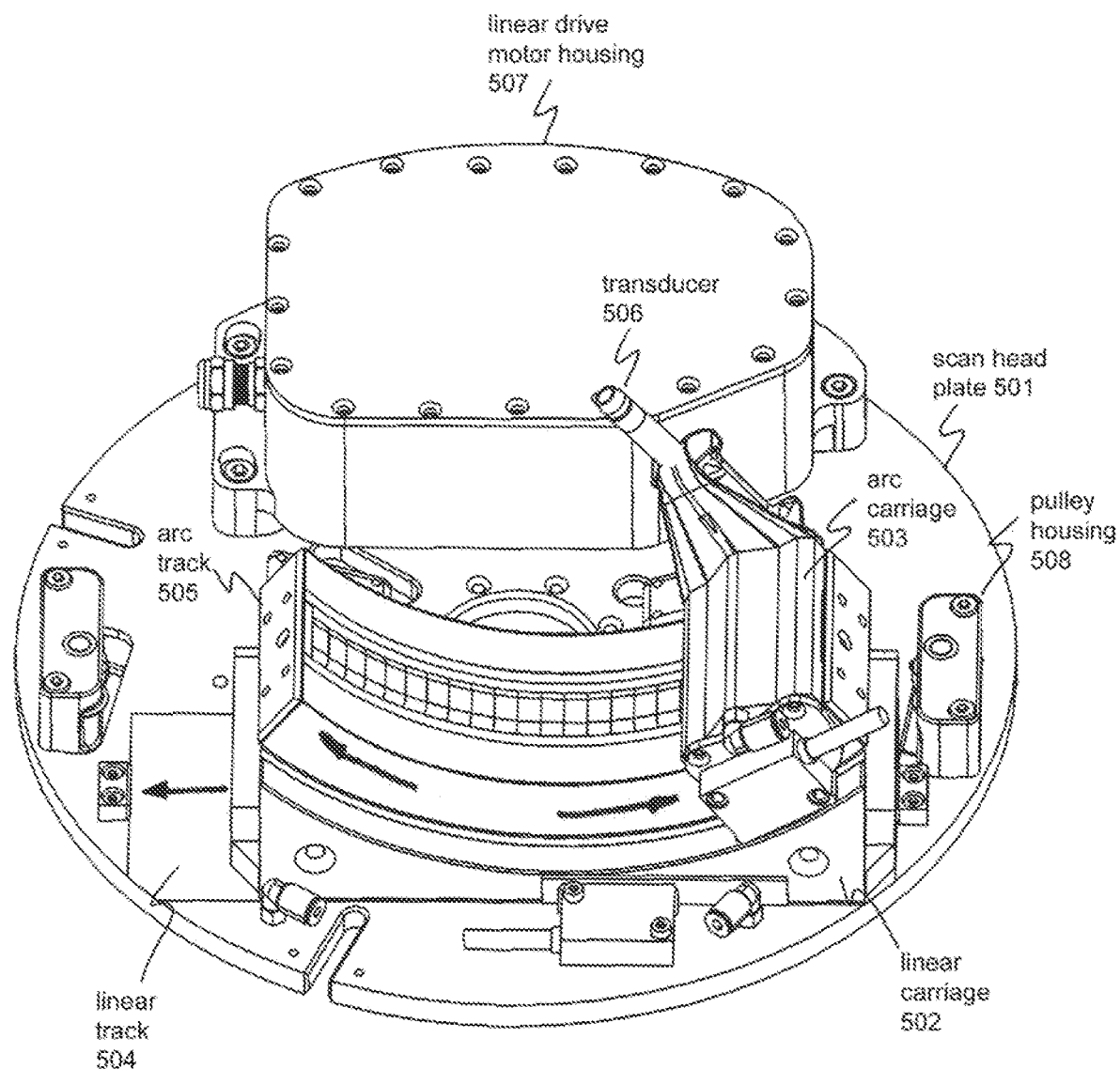
FIG. 5 illustrates a prior art scan head capable of combined motion arcuate and linear transducer motion.
Figure 6:
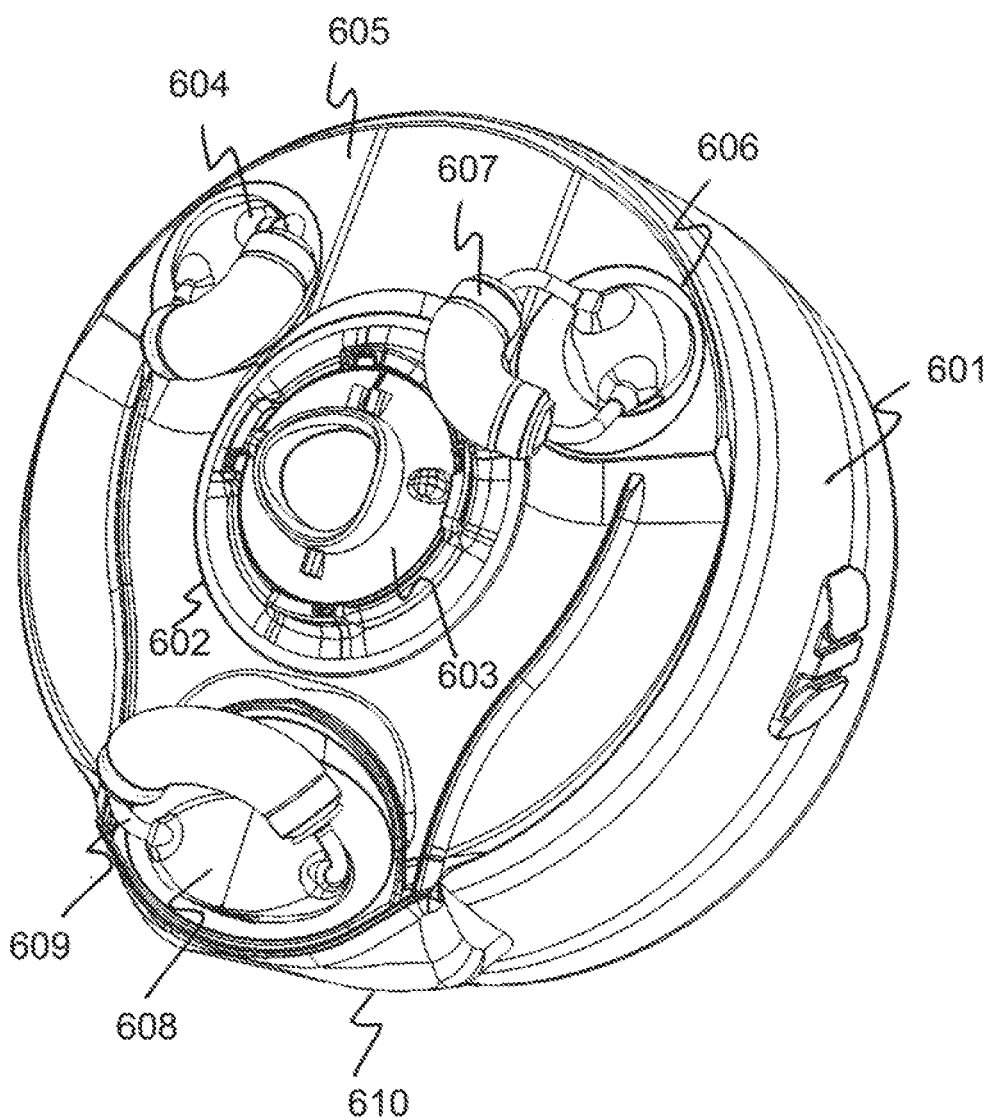
FIG. 6 is a schematic representation of a prior art a headrest for an eye scanning apparatus.

FIG. 5 illustrates a prior art scan head capable of linear motion, arcuate motion and combined linear and arcuate motion. This scan head was disclosed previously in U.S. Pat. No. 8,317,709. The scan head plate 501 replaces scan head mount structure 410 of FIG. 4. Scan head plate 501 serves as the platform for a computer controlled linear carriage 502 and arcuate carriage 503. Linear carriage 502 moves back and forth along linear guide track 504. Arcuate carriage 503 moves back and forth along arcuate guide track 505. In this view, arc carriage 503 is at the rightmost limit of its travel along arcuate guide track 505 and linear carriage 502 is also at the rightmost limit of its travel on linear guide track 504. As can be appreciated, the motions of arc carriage 503 and linear carriage 502 can be controlled independently. For example, arc carriage 503 can move along arcuate guide track 505 or be parked anywhere along arcuate guide track 505 while linear carriage 502 moves along linear guide track 504. As another example, linear carriage 502 can be stationary while arc carriage 503 moves back and forth along arcuate guide track 505 to execute a pure arc scan. When arc carriage 503 is stationary and linear carriage 502 is moved, this is referred to as a linear scan. When both arc carriage 503 and linear carriage 502 are moved, this is referred to as combined scan. In this configuration, arc carriage 503 is moved along arcuate guide track 505 by an induction motor as described in U.S. Pat. No. 8,758,252. Arc carriage 503 moves along arcuate guide track 505 on a fluid bearing which is also described in U.S. Pat. No. 8,758,252. Ultrasound scanning transducer 506 is mounted on arc carriage 503 and the axis of transducer 506 is aligned along the radius of curvature of arcuate guide track 505. Linear carriage 502 is moved along linear guide track 504 by a drive motor (not shown) housed in linear drive motor housing 507. This drive motor moves linear carriage 502 by a belt and pulley system (not shown except for typical pulley housing 508). Linear carriage 502 moves along linear guide track 504 on a fluid bearing similar to that used between arc carriage 503 and arcuate track 505. In operation, the scan head assembly of FIG. 5 is under water and is sealed from the x, y, z, beta positioner (shown in FIG. 4) by a sealing means behind the scan head plate. Thus the entire scanning mechanism is positioned with respect to an eye for scanning by the x, y, z, beta positioner shown in FIG. 5, while the actual acoustic imaging scan motion is implemented by one or both of the linear and arc carriages 502 and 503. The scan head assembly of FIG. 5 allows rapid independent linear and arcuate motion combinations of the transducer such that various scan geometries can be implemented to image not only the cornea, iris and anterior lens surface, but also the posterior lens surface, the sulcus, the ciliary body, the suprachoroidal space and the zonules that attach the lens to the ciliary body.

There is a special combined motion where the linear and arcuate motions are coordinated to produce a resultant arcuate motion of larger or smaller radius of curvature than the radius of curvature of the arcuate track. This combined motion is more completely is described in U.S. Pat. No. 8,317,709.

FIG. 6 is a schematic representation of an example of a headrest system suitable for the present invention. FIG. 6 shows the body of an ultrasonic imaging apparatus 601. A disposable eyepiece 603 is shown attached to an eyepiece retaining ring 602 which is permanently attached to the body of an ultrasound imaging apparatus 601. A headrest system is shown comprising a chin rest 608 and a two temple or forehead rests 604 and 606. Each of the chin rest 608 and two forehead rests 604 and 606 are comprised of a base plate such as 608, two connecting arms such as 609 and a central cushion such as 607. The base plate of each face rest subassembly can be moved around on a metallic surface 605 which is on the front side (patient side) of the body of the imaging device 601. The underside of each base plate includes a magnet (not shown) which maintains the base plate in contact with the metallic surface such that the face rest subassembly can be readily positioned anywhere on its corresponding metallic surface 605. When a light vacuum is applied, the face rest subassembly is locked onto the metallic surface and the cushion becomes rigid. The cushions may be constructed by filling a flexible, gas-impermeable containing bag or capsule with a granular material.

During the adjustment phase, the face rest subassemblies are moved around to best fit the patient's temples and chin. During this time, the cushions are maintained close the ambient atmospheric pressure. This allows the cushions of each face rest subassembly to conform to the temples and chin in such a way as to allow small adjustments of the head position to permit alignment with sealing devices or imaging components. For example, in the illustration of the ultrasonic scanner, the patient must make small adjustments to align his or her eye with a scanning reference beam while also maintaining a seal between his or her face and a flexible eyepiece.

When the head is aligned and the patient is comfortable, the vacuum system is pumped to a lower pressure, causing atmospheric pressure to force the face rest subassemblies into rigid contact with their corresponding metallic surfaces and to force the cushions' coverings to press firmly against the contained granular material. This simultaneously locks each face rest subassembly in place and locks the granular material in each cushion into place, maintaining the outer form of the cushion against subsequent movements of the head and holding the head rigidly in the desired position and alignment.

The cushions may be covered with a disposable paper, plastic or other covering to protect the cushions from patient's perspiration etcetera and to protect the patient from other patient's perspiration etcetera.

An advantage of this system is that each face rest subassembly is independently movable and the entire headrest system can be locked tight once the patient is in a comfortable position with respect to the scanner and with their eye properly positioned in the eyepiece. Another advantage of this system is the face rest subassemblies have a relatively low profile and this allows the operator to see around the cushions to determine if the patient is properly positioned and to see any problems that the patient may be having with the seal between their face and the eyepiece. Another advantage of this system is that any one of the face rest subassemblies may be removed if the operator deems this necessary. This headrest system is fully described in U.S. Pat. Nos. 8,510,883 and 8,732,878, which are herein incorporated by reference in their entirety.

An eyepiece serves to complete a continuous (substantially constant acoustic impedance) acoustic path for ultrasonic scanning, that path extending from the transducer to the surface of the patient's eye. The eyepiece also separates the water in which the patient's eye is immersed from the water in the chamber in which the positioner and scan head assemblies are immersed. Finally, when the patient is in position for a scan with his or her head firmly against the eye piece, the eyepiece provides a reference frame for the patient and helps the patient's head to remain steady during a scan. The eyepiece also must be able to pass optical wavelengths of light so that fixation targets can be used to focus the patient's eye in a desired focal state and alignment with respect to the eye's visual or optical axis.

An eyepiece system that satisfies these requirements typically consists of a mounting ring and a detachable eye piece. The mounting ring is attached to and is typically a permanent part of the main arc scanner assembly. The mounting ring has several attachment grooves which can accept attaching mechanisms on the eye piece. The eye piece is comprised of a base and a soft rubber or foam contoured face seal which is designed to seal against a typical human face around the eye that is to be scanned.

Figure 7:
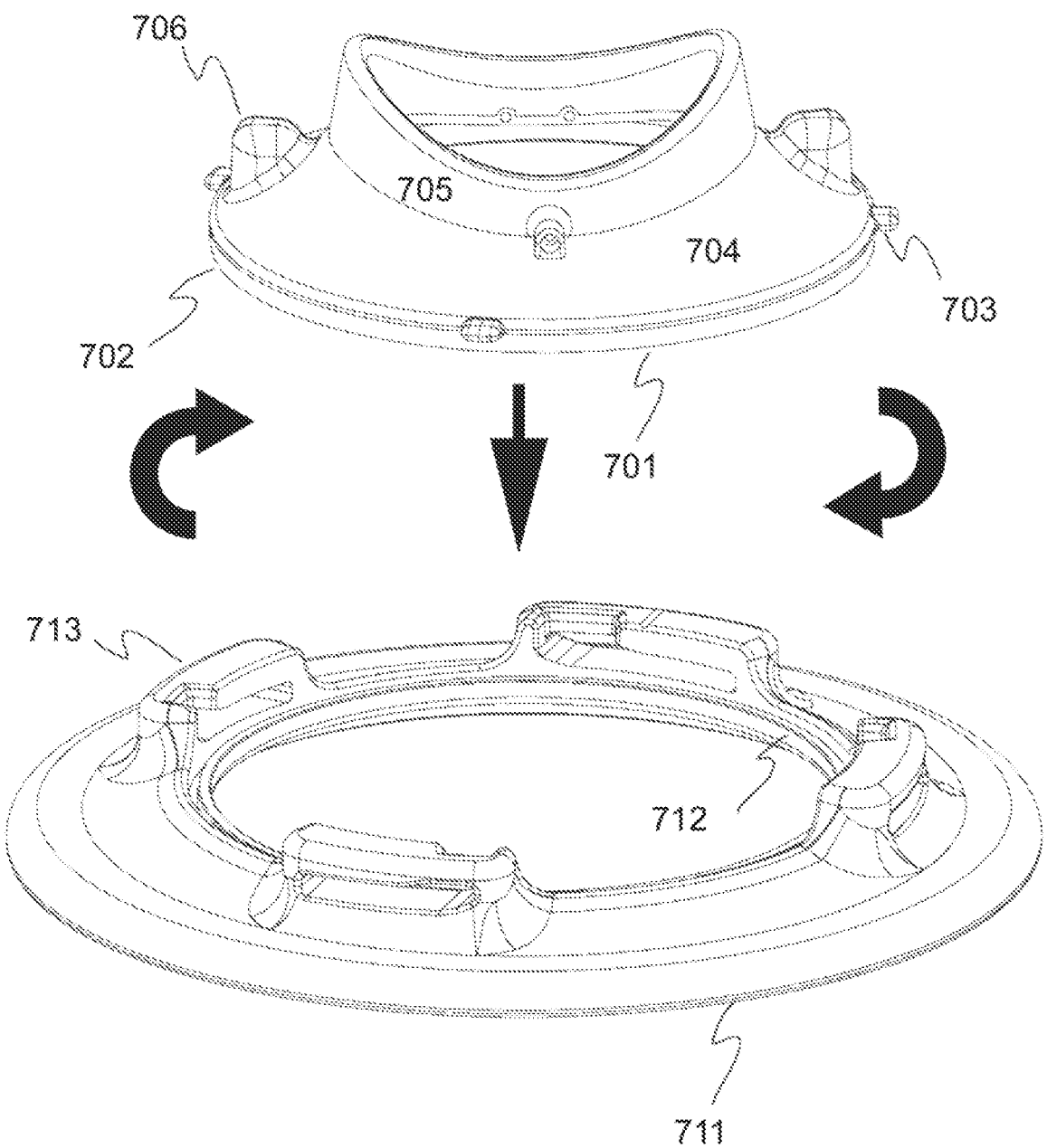
FIG. 7 illustrates a typical embodiment of a prior art eyepiece for an ultrasound eye scanner.

FIG. 7 illustrates a prior art embodiment of an eyepiece for an ultrasound scanner. The eyepiece consists of a mounting ring 711 and an eye piece 701. The mounting ring 711 is attached to the main scanner housing and is typically a permanent part of the main scanner assembly. The mounting ring 711 may be fabricated from aluminum, steel, plastic or the like to be compatible with the material of the main scanner housing. As shown here the mounting ring 711 has several attachment grooves 713 which can accept attaching mechanisms 703 on eye piece base 704. In this embodiment, the attaching mechanisms 703 are pushed down into the attachment grooves 713 and then rotated into position, using the thumb and finger protrusions 706, to form a mechanical connection that seals the eye piece base 704 against the mounting ring 711 to prevent water leakage. This is also known as a bayonet type connection. There is an additional sealing feature consisting of a groove 702 molded as part of the eye piece base 704 and a matching tongue 712 formed as part of the mounting ring 711. When the eye piece 701 is rotated into position with the mounting ring 711, the tongue and groove form a contact connection which compresses as the parts are rotated into position. Since the eye piece base 704 is typically made from a plastic, the compliance of the plastic further helps in forming a water tight seal. The eye piece 701 has a soft rubber or foam face seal 705 which is designed to seal against a typical human face around the eye that is to be scanned.

A sealed hygienic barrier (not shown) is formed as part of the eye piece 701 and is typically located where the soft rubber or foam face seal 705 is connected to the eye piece base 704 of eye piece 701.

As described previously, the eye piece typically includes a soft rubber or foam contoured face seal 705 which is designed to seal against a typical human face around the eye that is to be scanned. The contoured face seal 705 may also be made from a foam material impregnated with, for example, mineral oil, to provide a superior sealing action against a typical human face around the eye. This eye piece is more completely described U.S. Pat. No. 8,758,252.

Figure 8A:
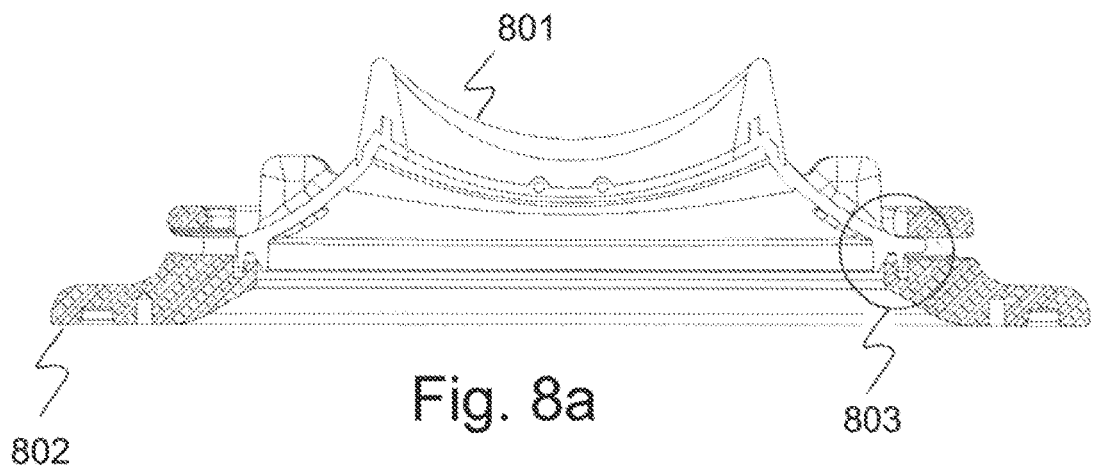
FIG. 8a illustrates a prior art sealing method for the eyepiece of FIG. 7.

FIG. 8 shows a section side view illustrating a prior art tongue and groove portion of the sealing method for the eye piece of FIG. 7. FIG. 8a shows an eyepiece consisting of a mounting ring 802 and an eye piece 801 is shown in sectional view with its tongue and groove sealing system indicated by callout 803.

Figure 8B:
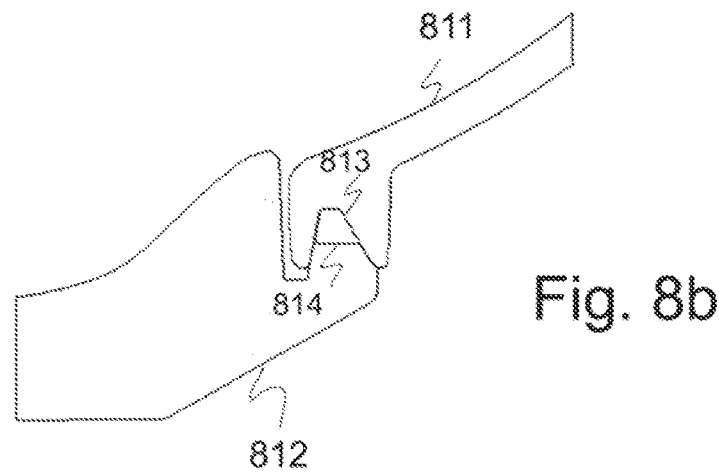

FIG. 8b illustrates a close up view of tongue and groove portion of the sealing method for the eye piece of FIG. 8a. The eye piece mounting ring 812 has a tongue 814 fabricated into mounting ring 812. The eye piece base 811 has a matching groove 813 molded into the eye piece base 811. When the eye piece base 811 is rotated into position with the mounting ring 812, the groove 813 compresses, deforming as necessary and form a tight seal with the tongue 814 as the parts are rotated into position.

The eye piece typically includes a soft rubber or foam contoured face seal which is designed to seal against a typical human face around the eye that is to be scanned. The contoured face seal may also be made from a foam material impregnated with, for example, mineral oil, to provide a superior sealing action against a typical human face around the eye.

A disposable eye piece system which includes the eye piece itself and other components includes a number of new features and construction details of the eye piece not previously disclosed, for example, in U.S. Pat. Nos. 8,758,252 or in 8,317,709.

Figure 9:
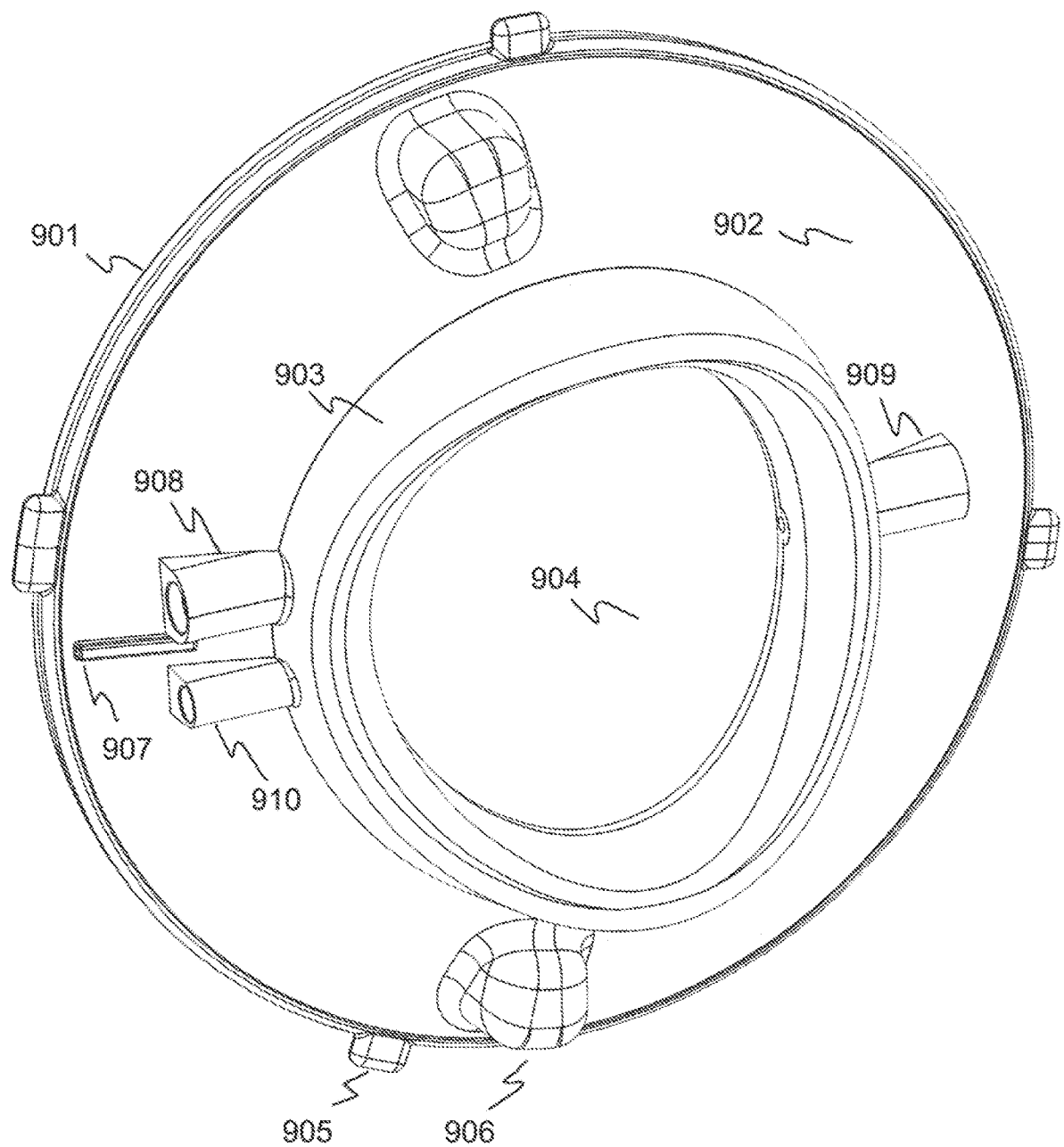
FIG. 9 is an isometric view of an advanced eye piece for a precision ultrasound scanning machine.

FIG. 9 is an isometric view of an advanced eye piece for a precision scanning machine. The eye piece 901 may be comprised of a plastic base 902 molded from a plastic such as ABS and a soft rubber conformable face seal 903 formed from a silicone thermo-plastic elastomer. The fill port 908, vent port 910 and drain port 909 are molded as part of the plastic base 902. The conformable face seal 903 is overmolded onto the plastic base 902, which includes fill port 908, vent port 910 and drain port 909, by a heat process typically applied to the conformable face seal 903. The plastic base 902 also includes attaching mechanisms 905 which attach the eye piece to the mounting ring which is typically attached to the main scanner housing; thumb and finger protrusions 906 used to rotate the eye piece into the mounting ring; indexing ridge 907 which prevents over-rotation of the eye piece as it is rotated into the mounting ring attached to the main scanner housing; and fill port 908, vent port 910 and drain port 909. Ports 908, 909 and 910 allow fluid flow through the eye piece base 901.

The eye piece is attached and sealed to a mounting ring which is, in turn, attached to the main scanner housing by a groove molded as part of the eye piece base 902 and a matching tongue formed as part of the mounting ring as further described in FIG. 9. The eye piece is rotated into position with the mounting ring where the tongue and groove form a contact connection which compresses and seals as the parts are rotated into position.

A sealed hygienic barrier membrane may be formed as part of the eye piece and, referring to FIG. 9, is typically located where the soft rubber face seal 903 is connected to the eye piece base 901. In some embodiments, this membrane is attached onto the plastic eye piece base 902 by an adhesive backing commonly used in medical disposable components. The thickness of the membrane is designed for transmission of light (such as the fixation targets shown in FIG. 3) and transmission of acoustic energy (emitted by the transducer and reflected by a component of the eye). The membrane is hermetically sealed to prevent saline solution, added between the patient's eye and membrane, from contaminating the distilled water in the scanning machine body (saline solution or tap water inside the machine body can corrode plastic, ceramic and metal components) and to prevent the distilled water in the machine body from contaminating the saline solution between the patient's eye and membrane. Eye piece membranes have been made from materials such as, for example, polyethylene, mylar, polypropylene; vinylidene chloride; polyvinylidene chloride; or DuraSeal (made by Diversified Biotech) which is polyethylene based material free of adhesives. A preferred material is medical grade polyethylene which has an acoustic impedance slightly higher than that of water (about 2.33 million kg/m$^2$-s compared to 1.54 million kg/m$^2$-s for water). The thickness of the membrane is preferably in the range of about 10 to about 30 microns. This thickness is a small part of an acoustic wavelength in water which is about 150 microns at 10 MHz and about 20 microns at 80 MHz.

The fill, drain and vent ports shown in FIG. 9 are used to fill and drain a saline solution in the space between the patient's eye and the membrane once the patient is in position for scanning. The fill, drain and vent ports are designed and sized for fast fill (to minimize the patient's time with their eye immersed in the saline solution), for venting of any bubbles that may form, for example, if the seal on the patient's head leaks or the patient pulls away from the machine, and for rapid draining of the saline solution back into the plastic saline bag after scanning is completed. As can be appreciated, the fill and vent ports are on the top or first end of the eye piece and the drain port is on the bottom or second end of the eye piece.

Figure 10:
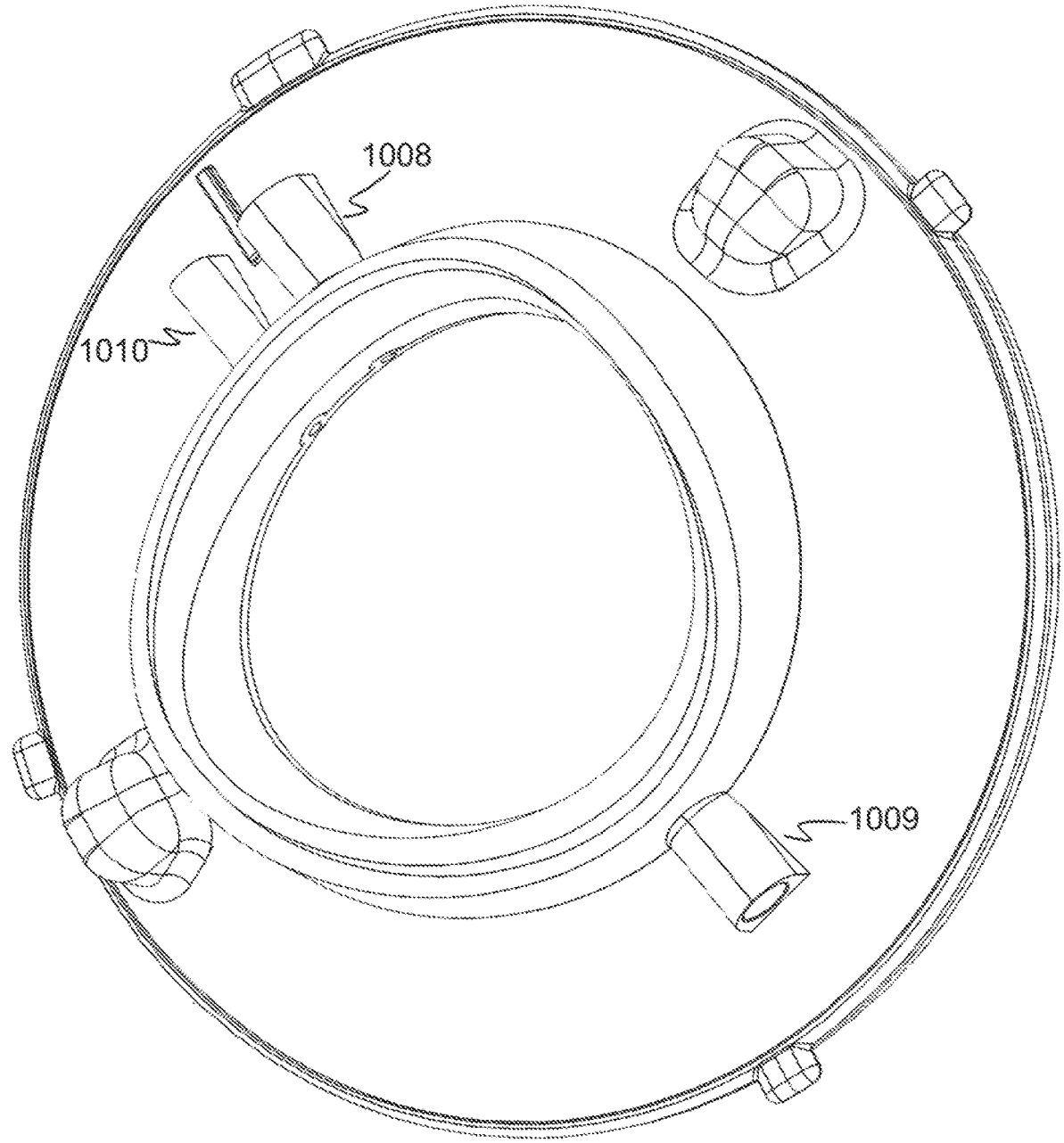
FIG. 10 is another isometric view of an advanced eye piece for a precision ultrasound scanning machine.
Figure 11:
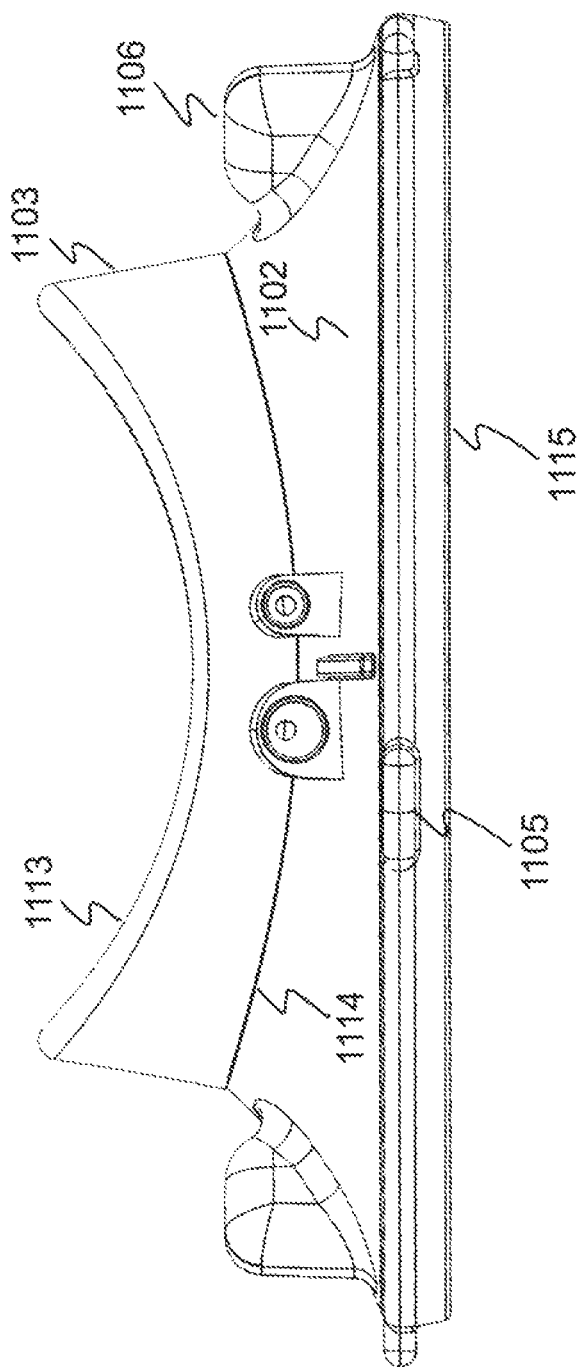
FIG. 11 is a side view of an advanced eye piece for a precision ultrasound scanning machine.

FIG. 10 is another isometric view of an advanced eye piece for a precision scanning machine illustrating another view of fill port 1008, vent port 1010 and drain port 1009. The fill port and vent port or ports are on the top of the conforming face seal while the drain port is on the bottom of the conforming face seal FIG. 11 is a side view of an advanced eye piece for a precision scanning machine. Plastic base 1102 includes attaching mechanisms 1105; eye seal groove 1115 for sealing; thumb and finger protrusions 1106 used to rotate the eye piece into the mounting ring; and the indexing ridge which is between the drain port and the vent port. For scanning, the patient's eye socket rests along surface 1113 of conformable face seal 1103.

The side of the eye piece that conforms to the patient's face along surface 1113 is the face seal portion of the eye piece. The side of the eye piece that engages the instrument body of the scanning device using attaching mechanisms 1105 is the instrument engagement portion of the eye piece.

A precision ultrasound scanner is comprised of a housing, such a shown schematically in FIG. 2, which includes the various sub-systems for operation. These include, for example, the positioning mechanism, scan head, transducer and transducer carriage, fluid module, computer module and ultrasound pulser module. Ultrasound scanner systems may comprise a disposable package which includes the components that are designed to be used on a single patient only. This disposable package is an integrated system that can be designed as a closed system wherein the system is maintained in a sterile condition from assembly until the eye piece is mated with the patient.

Figure 12:
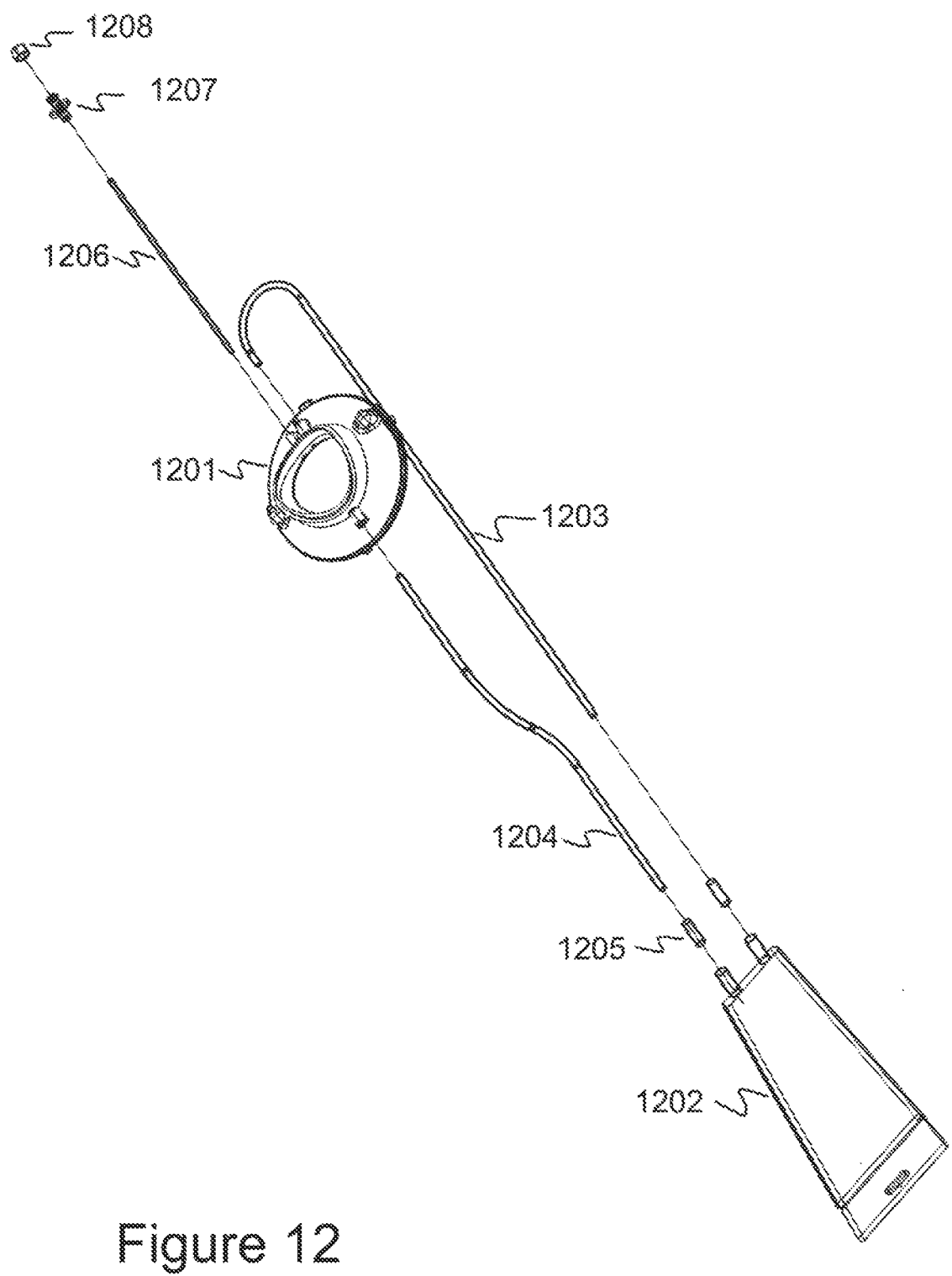
FIG. 12 is a schematic of an integrated disposable package, including an eye piece, for a precision ultrasound scanning machine.

FIG. 12 is a schematic of an integrated disposable package, including an eye piece, for a precision ultrasound scanning machine. The package is comprised of an eyepiece 1201, a plastic bag containing a sterile saline solution, a length of fill tubing 1203, a length of drain tubing 1204, a length of vent tubing 1206 including vent valve 1207 and vent cap or vent line clamp 1208 and various tubing-to-port connectors 1205.

A sealed hygienic barrier membrane is formed as part of the eye piece and is typically located and attached with adhesive where the soft rubber face seal is connected to the eye seal base of eye piece.

The fill, vent and drain tubing and connectors are typically solvent bonded to the three molded ABS ports in the eye piece base and to the ports on the plastic bag 1202. The fill, vent and drain tubing is typically a polyvinylchloride ("PVC") tubing and a preferred bonding solvent is cyclohexanone can be applied and set in approximately a 3 second bonding process.

A Radio Frequency ("RF") Identification ("ID") chip can be molded, preferably into the plastic base of the eye piece or, alternately into the conformable face seal of the eye piece. This RF ID chip can communicate with an RF pick-up device located on or inside the machine body. The RF ID chip can transfer information to the RF pick-up device to identify the specific patient associated with the eye piece and to record, for example, how many scans the patient has had using that eye seal and the date on which the scans were made.

Alternately, patient and eye piece information can be recorded on a bar code imprinted on the base of the eye piece. A bar code reader can be included as part of the scanning machine and, when read by the scanning machine, the information can be recorded in a data base in the computer that is part of the scanning machine.

The components of FIG. 12 form an integrated disposable package that can be assembled, packaged, transported and used while maintaining the eye piece and saline solution in a sterile condition by applying aseptic techniques at each stage of the assembly, packaging, transporting and scanning process. The above procedure can provide an eye piece, associated tubing internal diameters and saline solution as a system closed to ambient air from assembly through applying the eye seal to a patient immediately prior to scanning.

This closed system approach may include a protective cup positioned over the eye seal during packaging to protect the eye piece from distorting or damage during handling, shipping and storage. The protective cup an also be used for handling the eyepiece by the scanning physician or technician while the disposable package is removed from its shipping box and the eye piece is installed onto the scanning machine body.

The disposables package may also include several sterile wipes for use on the headrest cushions. As can be appreciated, all the disposable components can be packaged in a sealed plastic bag by aseptic techniques and the bag further packaged, for example, in an appropriately labeled cardboard box.

An eye piece may be wrapped and sealed in a plastic bag or membrane for shipping and storage, using sterile techniques. A further protective membrane can be applied to the eye piece surface (shown as item 1113 of FIG. 11) by a light adhesive. This further protective membrane can maintain the surface of conformable face seal (item 1013 of FIG. 11) and the interior chamber of the eye piece in a sterile condition. The interior chamber of the eye piece is the chamber in which saline solution is applied between the patient's eye and the internal eye piece membrane for providing a continuous acoustic and optical path between the patient's eye and the ultrasound transducer and fixation targets.

Figure 13:
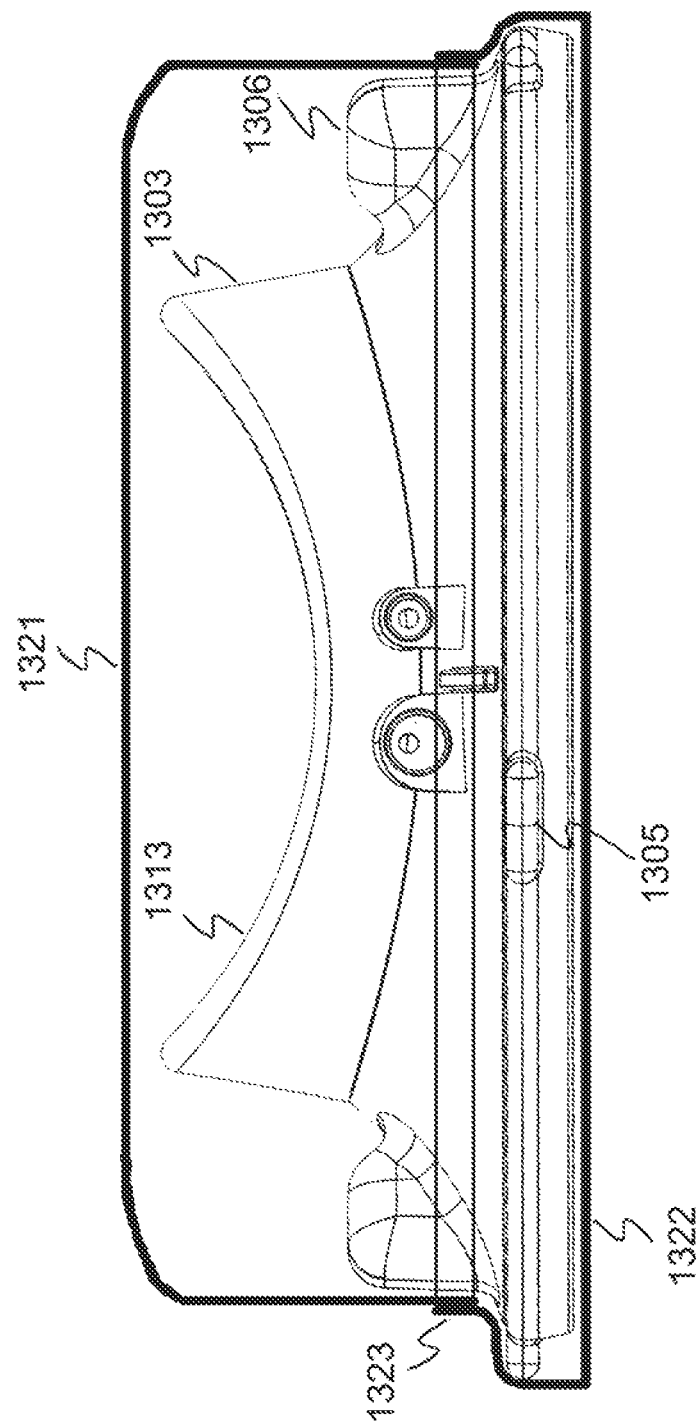
FIG. 13 is a schematic of a protective container for an eye piece suitable for a precision ultrasound scanning machine.

FIG. 13 is a schematic of a protective container for an eye piece suitable for a precision scanning machine. This protective container can be used in addition to or instead of the protective membrane described above. The protective container can be made out of a low-cost rigid plastic such as polystyrene for example. The protective container shown in FIG. 13 is made in two pieces. The top piece 1321 goes over the face seal side of the eye piece and attaches (by a screw thread for example), to a bottom piece 1322 which covers the bottom part of the eye piece that eventually attaches the eye piece to the scanning machine.

The protective shipping container 1) protects the eye piece from damage, human contact and exposure to ambient air during shipping and storage and 2) allows the scanning physician or technician to attach the eye piece to the scanning machine and prepare the eye piece for the patient without compromising the sterile condition of the interior chamber of the eye piece.

To attach the eyepiece 1303 to the scanning machine, the following steps may be taken: (1) by holding the top part of the protective container 1321, unscrew and remove the bottom part of the protective container 1322 at threaded joint 1323; the top part 1321 cannot rotate with respect to the eye piece 1303 as it is molded around and lightly held to thumb and finger protrusions 1306; (2) holding the top part of the protective container 1321, attach the eye piece to the mounting ring (item 711 of FIG. 7); the eye piece 1303 is still lightly held in top part 1321 of the protective container 1321 and eye piece 1303 cannot rotate with respect to the mounting ring during attachment, since top part 1321 is molded around and lightly held to thumb and finger protrusions 1306 of the eye piece 1303; (3) once the eye piece is attached to the mounting ring on the scanning machine, remove top part 1321 of the protective container by pulling it up and off the eye piece 1303; this now exposes the interior chamber of the eye piece to ambient air in which saline solution is applied between the patient's eye and the internal eye piece membrane; (4) once the eye piece is installed as described above, it is ready for use by the patient; the protective container may be manufactured in such a way as to be usable only once, for example by the threaded section of bottom part 1322 being made to break off when removed; alternately, the protective container may be shipped back to the manufacturer where it may be re-sterilized and used for another eye piece.

Exemplary steps for maintaining a sterile eye piece as a closed system from manufacture through use are: (1) assemble the eye piece; (2) sterilize the eye piece; (3) seal and package the eye piece using asterile techniques; (4) ship to the buyer; (5) store for eventual use; (6) just prior to use, remove the eye piece from its protective wrapping; (7) remove the bottom part of the protective container and attach the eye piece to the scanning machine; (8) remove the top part of the protective container and, if used, have the patient remove the further protective membrane from the conformable eye seal; (9) have the patient engage the eye piece in preparation for scanning.

A number of variations and modifications of the inventions can be used. As will be appreciated, it would be possible to provide for some features of the inventions without providing others.

The present disclosure, in various embodiments, includes components, methods, processes, systems and/or apparatus substantially as depicted and described herein, including various embodiments, sub-combinations, and subsets thereof. Those of skill in the art will understand how to make and use the present disclosure after understanding the present disclosure. The present disclosure, in various embodiments, includes providing devices and processes in the absence of items not depicted and/or described herein or in various embodiments hereof, including in the absence of such items as may have been used in previous devices or processes, for example for improving performance, achieving ease and\or reducing cost of implementation.

The foregoing discussion of the disclosure has been presented for purposes of illustration and description. The foregoing is not intended to limit the disclosure to the form or forms disclosed herein. In the foregoing Detailed Description for example, various features of the disclosure are grouped together in one or more embodiments for the purpose of streamlining the disclosure. This method of disclosure is not to be interpreted as reflecting an intention that the claimed disclosure requires more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate preferred embodiment of the disclosure.

Moreover though the description of the disclosure has included description of one or more embodiments and certain variations and modifications, other variations and modifications are within the scope of the disclosure, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed:

1. An eyepiece system for an ultrasonic scanning device, comprising:
   an ultrasonic scanning device having a radio frequency identification (RFID) reader;
   an eyepiece base having a face seal portion, said face seal portion defining a partially enclosed volume, said face seal portion having a first end and a second end disposed opposite of said first end;
   a fill port disposed proximate to said first end of said face seal portion, said fill port providing fluid communication between said partially enclosed volume and an ambient environment;
   a vent port disposed proximate to said first end of said face seal portion, said vent port providing fluid communication between said partially enclosed volume and said ambient environment;
   a drain port disposed proximate to said second end of said face seal portion, said drain port providing fluid communication between said partially enclosed volume and said ambient environment; and
   a RFID chip disposed on said eyepiece base, wherein the RFID chip is configured to transmit scan record information to said RFID reader via a wireless communication protocol, and wherein said scan record information includes a number of scans using said eyepiece base.

2. The eyepiece system of claim 1, further comprising:
   a second vent port disposed on said eyepiece base, said vent port providing fluid communication between said partially enclosed volume and said ambient environment.

3. The eyepiece system of claim 2, wherein said second vent port is disposed proximate to said first end of said face seal portion.

4. The eyepiece system of claim 1, further comprising:
   a plurality of protrusions disposed on said eyepiece base, said plurality of protrusions providing a location for an operator to rotate said eyepiece relative to said ultrasonic scanning device.

5. The eyepiece system of claim 1, further comprising:
   a sealed hygienic barrier member disposed on said eyepiece base.

6. The eyepiece system of claim 1, further comprising:
   a groove disposed about a circumference of said eyepiece base, said groove corresponding to a tongue disposed on said ultrasonic scanning device.

7. The eyepiece system of claim 1, further comprising:
   a protective membrane disposed on said face seal portion of said eyepiece base, wherein said protective membrane and said face seal portion form an enclosed volume.

8. A method of transmitting information from an eyepiece to an ultrasonic scanning device, comprising:
   providing an ultrasonic scanning device having a radio frequency identification (RFID) reader;
   providing an eyepiece base having a face seal portion, said face seal portion defining a partially enclosed volume, said face seal portion having a first end and a second end disposed opposite of said first end;
   providing a fill port on said face seal portion proximate to said first end of said face seal portion, said fill port providing fluid communication between said partially enclosed volume and an ambient environment;
   providing a vent port on said face seal portion proximate to said first end of said face seal portion, said vent port providing fluid communication between said partially enclosed volume and said ambient environment;
   providing a drain port on said face seal portion proximate to said second end of said face seal portion, said drain port providing fluid communication between said partially enclosed volume and said ambient environment;
   providing a RFID chip disposed on said eyepiece base, wherein said RFID chip is configured to store scan record information including a number of scans using said eyepiece base; and
   coupling said RFID chip of said eyepiece base to said RFID reader of said ultrasonic scanning device via a wireless communication protocol so that said RFID chip can transmit said scan record information to said RFID reader.

9. The method of claim 8, further comprising:
   providing a second vent port on said eyepiece base proximate to said first end of said face seal portion, said vent port providing fluid communication between said partially enclosed volume and said ambient environment.

10. The method of claim 8, further comprising:
    providing a plurality of protrusions disposed on said eyepiece base, said plurality of protrusions providing a location for an operator to rotate said eyepiece relative to said ultrasonic scanning device.

11. The method of claim 8, further comprising:
    providing a sealed hygienic barrier member disposed on said eyepiece base;
    providing a groove disposed about a circumference of said eyepiece base, said groove corresponding to a tongue disposed on said ultrasonic scanning device; and
    providing a protective membrane disposed on said face seal portion of said eyepiece base, wherein said protective membrane and said face seal portion form an enclosed volume.

12. A device comprising:
    an eyepiece for use in imaging an ocular feature of a patient wherein the eyepiece is comprised of a face seal portion and an instrument engagement portion; and
    a protective container engaged with and/or containing the eyepiece, wherein the protective container is removably attached to the eyepiece to enable an operator to attach the instrument engagement portion of the eyepiece to a scanning machine prior to removal of the protective container from face seal portion of the eyepiece, wherein the protective container comprises a first rigid part and a second rigid part, wherein the first rigid part covers the face seal portion of the eyepiece and the second rigid part covers the instrument engagement portion of the eyepiece, wherein the first rigid part removably engages the second rigid part to form the protective container enclosing the eyepiece and wherein the protective container is at least substantially closed to an ambient environment.

13. A method, comprising:
providing an eyepiece conformable to a face of a patient for use in imaging an ocular feature of the patient and a protective container engaged with and/or containing the conformable eyepiece wherein the protective container comprises a first part protecting the face seal portion of the conformable eyepiece and a second part covering the instrument engagement portion of the conformable eyepiece;
disengaging the second part of the protective container, wherein after disengaging, the first part remains engaged with the conformable eyepiece while the second part does not;
engaging the instrument engagement portion of the conformable eyepiece with a scanning machine, wherein the first part and the conformable eyepiece do not move independently during engaging; and
disengaging the first part from the conformable eyepiece after the conformable eyepiece is engaged with the scanning machine.

14. The method of claim 13, wherein the protective container is removably attached to the conformable eyepiece to enable an operator to engage the conformable eyepiece with a scanning machine prior to removal of the protective container from the conformable eyepiece.

15. The method of claim 13, wherein during engaging an operator does not touch the conformable eyepiece.

16. The method of claim 13, wherein the first part is threaded to the conformable eyepiece.

17. The method of claim 13, wherein the first part is disengaged from the conformable eyepiece by linearly moving the first part away from the conformable eyepiece.

* * * * *